United States Patent
Kensey et al.

(10) Patent No.: US 6,745,615 B2
(45) Date of Patent: *Jun. 8, 2004

(54) DUAL RISER/SINGLE CAPILLARY VISCOMETER

(75) Inventors: Kenneth Kensey, Chester Springs, PA (US); William N. Hogenauer, Gilbertsville, PA (US); Sangho Kim, Philadelphia, PA (US); Young Cho, Cherry Hill, NJ (US)

(73) Assignee: Rheologics, Inc., Exton, PA (US)

( * ) Notice: Subject to any disclaimer, the term of this patent is extended or adjusted under 35 U.S.C. 154(b) by 331 days.

This patent is subject to a terminal disclaimer.

(21) Appl. No.: 09/973,639

(22) Filed: Oct. 9, 2001

(65) Prior Publication Data

US 2002/0040196 A1 Apr. 4, 2002

Related U.S. Application Data

(63) Continuation of application No. 09/573,267, filed on May 18, 2000, now Pat. No. 6,402,703, which is a continuation-in-part of application No. 09/439,795, filed on Nov. 12, 1999, now Pat. No. 6,322,524, which is a continuation-in-part of application No. 08/919,906, filed on Aug. 28, 1997, now Pat. No. 6,019,735.

(51) Int. Cl.[7] ............................................... G01N 11/04
(52) U.S. Cl. .................... 73/54.04; 73/54.01; 73/54.05; 73/54.06
(58) Field of Search ......................... 73/54.01, 54.02, 73/54.04, 54.05, 54.06; 600/406, 573, 574, 587

(56) References Cited

U.S. PATENT DOCUMENTS 1,810,992 A * 6/1931 Dallwitz-Wegner ........ 73/54.01
1,963,011 A * 6/1934 Albersheim et al. ....... 73/54.11
2,095,282 A * 10/1937 Payne ........................ 73/54.04

(List continued on next page.)

FOREIGN PATENT DOCUMENTS

DE   31 38514 A1   4/1983
EP   0 654 286 A1   12/1994

(List continued on next page.)

OTHER PUBLICATIONS

A Capillary Viscometer with Continuously Varying Pressure Head, Maron, et al., vol. 25, No. 8, Aug. 1954.

(List continued on next page.)

*Primary Examiner*—Hezron Williams
*Assistant Examiner*—David A. Rogers
(74) *Attorney, Agent, or Firm*—Caesar, Rivise, Bernstein, Cohen & Pokotilow, Ltd.

(57) ABSTRACT

A blood viscosity measuring system and methods for measuring blood viscosity monitors the change in height of one of two, oppositely-moving, columns of blood from the circulating blood of a patient and, given the dimensions of a capillary tube through which the blood flows and by detecting a single blood position of the other oppositely-moving column, determines the blood viscosity over a range of shears, especially low shears. The system includes a tube set (disposable or non-disposable) that includes a pair of riser tubes, a capillary tube of predetermined dimensions that is coupled between the riser tubes (or that forms a portion of one riser tube) and a valve mechanism for controlling the circulating flow of blood from the patient into the riser tubes. A sensor monitors the movement of one of the columns of blood in one of the riser tubes and a single point detector detects a single blood position of the other column of blood and an associated microprocessor analyzes this movement and single point, along with the predetermined dimensions of the capillary tube, to determine the viscosity of the patient's circulating blood.

30 Claims, 23 Drawing Sheets

U.S. PATENT DOCUMENTS

| | | | | |
|---|---|---|---|---|
| 2,095,324 A | * | 10/1937 | Simons | 73/54.04 |
| 2,343,061 A | * | 2/1944 | Irany | 73/54.04 |
| 2,696,734 A | | 12/1954 | Brunstrum et al. | |
| 2,700,891 A | * | 2/1955 | Shafe | 73/54.06 |
| 2,934,944 A | | 5/1960 | Eolkin | |
| 3,071,961 A | | 1/1963 | Heigl et al. | |
| 3,116,630 A | | 1/1964 | Piros | |
| 3,137,161 A | | 6/1964 | Lewis et al. | |
| 3,138,950 A | | 6/1964 | Welty et al. | |
| 3,277,694 A | * | 10/1966 | Cannon et al. | 73/54.07 |
| 3,286,511 A | | 11/1966 | Harkness | |
| 3,342,063 A | | 9/1967 | Smythe et al. | |
| 3,435,665 A | | 4/1969 | Tzentis | |
| 3,520,179 A | * | 7/1970 | Reed | 73/54.04 |
| 3,604,247 A | | 9/1971 | Gramaln et al. | |
| 3,666,999 A | | 5/1972 | Moreland, Jr. et al. | |
| 3,680,362 A | | 8/1972 | Geerdes et al. | |
| 3,699,804 A | * | 10/1972 | Gassmann et al. | 73/54.07 |
| 3,713,328 A | * | 1/1973 | Aritomi | 73/54.08 |
| 3,720,097 A | | 3/1973 | Kron | |
| 3,782,173 A | | 1/1974 | Van Vessem et al. | |
| 3,839,901 A | | 10/1974 | Finkle et al. | |
| 3,853,121 A | | 12/1974 | Mizrachy et al. | |
| 3,864,962 A | * | 2/1975 | Stark et al. | 73/54.07 |
| 3,908,441 A | | 9/1975 | Virloget | |
| 3,911,728 A | | 10/1975 | Fixot | |
| 3,952,577 A | | 4/1976 | Hayes et al. | |
| 3,967,934 A | | 7/1976 | Seitz et al. | |
| 3,990,295 A | | 11/1976 | Renovanz et al. | |
| 3,999,538 A | | 12/1976 | Philpot, Jr. | |
| 4,028,929 A | * | 6/1977 | Bohm | 73/54.04 |
| 4,083,363 A | | 4/1978 | Philpot, Jr. | |
| 4,149,405 A | | 4/1979 | Ringrose | |
| 4,165,632 A | | 8/1979 | Weber et al. | |
| 4,193,293 A | | 3/1980 | Cavallari | |
| 4,207,870 A | | 6/1980 | Eldridge | |
| 4,302,965 A | | 12/1981 | Johnson et al. | |
| 4,341,111 A | | 7/1982 | Husar | |
| 4,417,584 A | | 11/1983 | Cathignol et al. | |
| 4,426,878 A | | 1/1984 | Price et al. | |
| 4,432,761 A | | 2/1984 | Dawe | |
| 4,461,830 A | | 7/1984 | Philpot, Jr. | |
| 4,517,830 A | | 5/1985 | Gunn et al. | |
| 4,519,239 A | | 5/1985 | Kiesewetter et al. | |
| 4,554,821 A | | 11/1985 | Kiesewetter et al. | |
| H93 H | | 7/1986 | Matta et al. | |
| 4,616,503 A | | 10/1986 | Plungis et al. | |
| 4,637,250 A | | 1/1987 | Irvine, Jr. et al. | |
| 4,643,021 A | | 2/1987 | Mattout | |
| 4,680,957 A | | 7/1987 | Dodd | |
| 4,680,958 A | | 7/1987 | Ruelle et al. | |
| 4,750,351 A | | 6/1988 | Ball | |
| 4,856,322 A | | 8/1989 | Langrick et al. | |
| 4,858,127 A | | 8/1989 | Kron et al. | |
| 4,884,577 A | | 12/1989 | Merrill | |
| 4,899,575 A | | 2/1990 | Chu et al. | |
| 4,947,678 A | | 8/1990 | Hori et al. | |
| 5,099,698 A | | 3/1992 | Kath et al. | |
| 5,142,899 A | * | 9/1992 | Park et al. | 73/54.04 |
| 5,181,415 A | | 1/1993 | Esvan et al. | |
| 5,222,497 A | | 6/1993 | Ono | |
| 5,224,375 A | * | 7/1993 | You et al. | 73/54.08 |
| 5,257,529 A | | 11/1993 | Taniguchi et al. | |
| 5,271,398 A | | 12/1993 | Schlain et al. | |
| 5,272,912 A | * | 12/1993 | Katsuzaki | 73/54.08 |
| 5,327,778 A | | 7/1994 | Park | |
| 5,333,497 A | * | 8/1994 | Br nd Dag A. et al. | 73/219 |
| 5,365,776 A | | 11/1994 | Lehmann et al. | |
| 5,421,328 A | | 6/1995 | Bedingham | |
| 5,447,440 A | | 9/1995 | Davis et al. | |
| 5,491,408 A | | 2/1996 | Rousseau | |
| 5,494,639 A | | 2/1996 | Grzegorzewski | |
| 5,629,209 A | | 5/1997 | Braun, Sr. et al. | |
| 5,686,659 A | | 11/1997 | Neel et al. | |
| 5,725,563 A | | 3/1998 | Klotz | |
| 5,792,660 A | | 8/1998 | Spillert et al. | |
| 5,837,885 A | | 11/1998 | Goodbread et al. | |
| 6,019,735 A | | 2/2000 | Kensey et al. | |
| 6,039,078 A | | 3/2000 | Tamari | |
| 6,077,234 A | | 6/2000 | Kensey | |
| 6,152,888 A | | 11/2000 | Kensey et al. | |
| 6,158,271 A | * | 12/2000 | de Corral | 73/54.05 |
| 6,193,667 B1 | | 2/2001 | Kensey | |
| 6,200,277 B1 | | 3/2001 | Kensey | |
| 6,261,244 B1 | | 7/2001 | Kensey et al. | |
| 6,322,524 B1 | | 11/2001 | Kensey et al. | |
| 6,428,488 B1 | | 8/2002 | Kensey et al. | |

FOREIGN PATENT DOCUMENTS

| | | |
|---|---|---|
| FR | 2 510 257 | 1/1983 |
| WO | WO 92/15878 | 9/1992 |
| WO | WO 94/20832 | 9/1994 |
| WO | WO 99/10724 | 3/1999 |

OTHER PUBLICATIONS

Colloid Symposium Monograph, P. Glesy, et al., vol. V, p. 253, 1928.

Kolloid–Zeitschrift, Prof. Dr. Wolfgang Ostwald, Band XLI, Leipzig University, 1927.

Kensey, et al., Effects of whole blood viscosity on atherogenesis, Jnl. Of Invasive Cardiol. V. 9, 17, 1997.

Ernst, et al., Cardiovascular Risk Factors & Hemorrheology: Physical Fitness, Stress & Obesity, Atheros. V. 59, 263–269, 1986.

Levenson, et al., Cigarette Smoking & Hypertension, Atherosclerosis V, 7, 572–577, 1987.

Rillaerts, et al., Blood viscosity in Human Obesity; relation to glucose Tolerance and Insulin Status, Internl Jnl. Of Obesity, V. 13, 739–741, 1989.

Rosenson, R., Viscosity & Ischemic Heart Disease, Jnl. Of Vascular Medicine & Biol., V. 4, 206–212, 1993.

Letcher, et al., Direct Relationship Between Blood Pressure & Blood Viscosity in Normal & Hypertensive Subjects, Am. Jnl of Med. V. 70, 1195–1203, Jun. 1981.

Zwick, K.J., The Fluid Mechanics of Bonding with Yield Stress Exposies, Dissortation, Un. Of Penn., PA, USA, 1–142, 1996.

Yarnell, et al., Fibrinogen, viscosity & White Blood Cell Count are Major Risk Factors for Ischemic Heart Disease, Circulation, V. 83, No. 3, Mar. 1991.

Tangney, et al., Postprandial changes in Plasma & Serum Viscosity & Plasma Lipids & Lipoproteins after an acute test meal, Am. Jnl. Of Clin. Nutrition V. 65, 36–40, 1997.

Seplowitz, et al., Effects of Lipoproteins on Plasma Viscosity, Atherosclerosis, V. 38, 89–95, 1981.

Rosenson, et al., Hyperviscosity Syndrome in Hypercholesterolemic Patient with Primary Billiary Cirrhosis, Gastroenterology, V. 98, No. 5, 1990.

Lowe, et al., Blood Viscosity & Risk of Cardiovascular Events: the Edinburg Artery Study, British Jnl. Of Haematology, V. 96, 168–173, 1997.

Koenig, W., Blood Rheology Assoc. with Cardiovascular Risk Factors & Chronic Cardiovascular Diseases: Results of an Epidemiologic Cross Sectional Study, Am. Coll. Of Angiology, Paradise Is., Bahamas, Oct. 1997.

Hell, K., Importance of Blood Viscoelasticity in Arteriosclerosis, Internl Coll. Of Angiology, Montreux, Switzerland, Jul. 1987.

Delaunois, A., Thermal method for Continuous Blood velocity Measurements in Large Blood Vessels & Cardiac Output Determination, Medical & Biological Engineering, Mar. 1973, V. 11, 201–205.

Nerem, et al., Fluid Mechanics in Atherosclerosis, Handbook of Bioengineering, Chp. 21, 20.24 to 21.22.

Litt, et al., Theory & Design of Disposable Clinical Blood Viscometer, Biorheology, V. 25, 697–712, 1988.

Cooke, et al., Automated Measurement of Plasma Viscosity by Capillary Viscometer, J. Clin. Path., vol. 341, 1213–1216, 1988.

Jiminez, et al., A novel computerized Viscometer/rheometer, Rev. sci. Instrum. V. 65, (1), 229–241, Jan. 1994.

Harkness, A New Instrument for Measurement of Plasma–Viscosity, Med. & Biol. Engineering, Sep. 1976.

Pringle, et al., Blood Viscosity & Raynaud's Disease, The Lancet, May 1965.

Walker, et al., Measurement of Blood Viscosity using a conicylindrical viscometer, Med. & Biol. Engineering, Sep. 1976.

Oguraa, et al., Measurement of Human Red Blood Cell Deformability using a Single Micropore on a Thin Si3N4 Film, IEEE Transactions on Biomedical Engineering, V. 38, No. 9, Aug. 1991.

Hausler, et al., A Newly Designed Oscillating Viscometer for Blood Viscosity Measurements, 1999 V. 33, No. 4, Biorheology, p. 397–404.

Martin, et al., Apparent Viscosity of Whole Human Blood at Various Hydrostatic Pressures I. Studies on Anticoagulated Blood Employing new Capillary Viscometer, Biorheology 3–12, V. 11, 1978.

Rheinhard, et al., Rheologic Measurements on Small Samples with a New Capillary Viscometer, J.Lab. And Clin. Med., 921–931, Dec. 1984.

Chmiel, A New Capillary Viscometer for Clinical use, Biorheology, 301–307, V. 12, 1979.

Pall Corporation, Pall BPF4 High Efficiency Leukocyte Removal Blood Processing Filter System, Pall Biomedical Products Corporation 1993.

Qamar, et al., The Goldman Algorithm Revisited: Prospective E#valuation of Computer Derived Algorithm Vs. Unaided Physician Judgement in Suspected Acute Myocardial Inf., AM. Hrt J. 138, V. 4, 705–709, 1999.

Leonhardt, et al., Studies of Plasma Viscosity in Primary Hyperlipoproteinaemia, Atherosclerosis, V.28, 29–40, 1977.

* cited by examiner

DUAL RISER/SINGLE CAPILLARY VISCOMETER

RELATED APPLICATIONS

This application is a Continuation application of Co-Pending application Ser. No. 09/573,267 (now U.S. Pat. No. 6,402,703). filed on May 18, 2000 which in turn is a Continuation-in-Part of application Ser. No. 09/439,795 (now U.S. Pat. No. 6,322,524), filed on Nov. 12, 1999, both of which are entitled DUAL RISER/SINGLE CAPILLARY VISCOMETER, which in turn is a Continuation-in-Part application of application Ser. No. 08/919,906, filed Aug. 28, 1997 now U.S. Pat. No. 6,019,735, entitled VISCOSITY MEASURING APPARATUS AND METHOD OF USE, all of which are assigned to the same Assignee as the present invention, namely, Rheologics Inc., and all of whose entire disclosures are incorporated by reference herein.

BACKGROUND OF THE INVENTION

This invention relates generally to an apparatus and method for measuring the viscosity of liquids, and more particularly, an apparatus and methods for measuring the viscosity of the blood of a living being in-vivo and over a wide range of shears.

The importance of determining the viscosity of blood is well-known. *Fibrogen, Viscosity and White Blood Cell Count Are Major Risk Factors for Ischemic Heart Disease*, by Yarnell et al., Circulation, Vol. 83, No. 3, March 1991; *Postprandial Changes in Plasma and Serum Viscosity and Plasma Lipids and Lipoproteins After an Acute Test Meal*, by Tangney, et al., American Journal for Clinical Nutrition, 65:36–40, 1997; *Studies of Plasma Viscosity in Primary Hyperlipoproteinaemia*, by Leonhardt et al., Atherosclerosis 28,29–40, 1977; *Effects of Lipoproteins on Plasma Viscosity*, by Seplowitz, et al., Atherosclerosis 38, 89–95, 1981; *Hyperviscosity Syndrome in a Hypercholesterolemic Patient with Primary Biliary Cirrhosis*, Rosenson, et al., Gastroenterology, Vol. 98, No. 5, 1990; *Blood Viscosity and Risk of Cardiovascular Events:the Edinburgh Artery Study*, by Lowe et al., British Journal of Hematology, 96, 168–171, 1997; *Blood Rheology Associated with Cardiovascular Risk Factors and Chronic Cardiovascular Diseases: Results of an Epidemiologic Cross-Sectional Study*, by Koenig, et al., Angiology, The Journal of Vascular Diseases, November 1988; *Importance of Blood Viscoelasticity in Arteriosclerosis*, by Hell, et al., Angiology, The Journal of Vascular Diseases, June, 1989; *Thermal Method for Continuous Blood-Velocity Measurements in Large Blood Vessels, and Cardiac-Output Determination*, by Delanois, Medical and Biological Engineering, Vol. 11, No. 2, March 1973; *Fluid Mechanics in Atherosclerosis*, by Nerem, et al., Handbook of Bioengineering, Chapter 21, 1985.

Much effort has been made to develop apparatus and methods for determining the viscosity of blood. *Theory and Design of Disposable Clinical Blood Viscometer*, by Litt et al., Biorheology, 25, 697–712, 1988; *Automated Measurement of Plasma Viscosity by Capillary Viscometer*, by Cooke, et al., Journal of Clinical Pathology 41, 1213–1216, 1988; *A Novel Computerized Viscometer/Rheometer* by Jimenez and Kostic, Rev. Scientific Instruments 65, Vol 1, January 1994; *A New Instrument for the Measurement of Plasma-Viscosity*, by John Harkness, The Lancet, pp. 280–281, Aug. 10, 1963; *Blood Viscosity and Raynaud's Disease*, by Pringle, et al., The Lancet, pp. 1086–1089, May 22, 1965; *Measurement of Blood Viscosity Using a Conicylindrical Viscometer*, by Walker et al., Medical and Biological Engineering, pp. 551–557, September 1976.

One reference, namely, *The Goldman Algorithm Revisited: Prospective Evaluation of a Computer-Derived Algorithm Versus Unaided Physician Judgment in Suspected Acute Myocardial Infarction*, by Qamar, et al., Am Heart J 138(4):705–709, 1999, discusses the use of the Goldman algorithm for providing an indicator to acute myocardial infarction. The Goldman algorithm basically utilizes facts from a patient's history, physical examination and admission (emergency room) electrocardiogram to provide an AMI indicator.

In addition, there are a number of patents relating to blood viscosity measuring apparatus and methods. See for example, U.S. Pat. No. 3,342,063 (Smythe et al.); U.S. Pat. No. 3,720,097 (Kron); U.S. Pat. No. 3,999,538 (Philpot, Jr.); U.S. Pat. No. 4,083,363 (Philpot); U.S. Pat. No. 4,149,405 (Ringrose); U.S. Pat. No. 4,165,632 (Weber, et. al.); U.S. Pat. No. 4,517,830 (Gunn, deceased, et. al.); U.S. Pat. No. 4,519,239 (Kiesewetter, et. al.); U.S. Pat. No. 4,554,821 (Kiesewetter, et. al.); U.S. Pat. No. 4,858,127 (Kron, et. al.); U.S. Pat. No. 4,884,577 (Merrill); U.S. Pat. No. 4,947,678 (Hori et al.); U.S. Pat. No. 5,181,415 (Esvan et al.); U.S. Pat. No. 5,257,529 (Taniguchi et al.); U.S. Pat. No. 5,271,398 (Schlain et al.); and U.S. Pat. No. 5,447,440 (Davis, et. al.).

The Smythe '063 patent discloses an apparatus for measuring the viscosity of a blood sample based on the pressure detected in a conduit containing the blood sample. The Kron '097 patent discloses a method and apparatus for determining the blood viscosity using a flowmeter, a pressure source and a pressure transducer. The Philpot '538 patent discloses a method of determining blood viscosity by withdrawing blood from the vein at a constant pressure for a predetermined time period and from the volume of blood withdrawn. The Philpot '363 patent discloses an apparatus for determining blood viscosity using a hollow needle, a means for withdrawing and collecting blood from the vein via the hollow needle, a negative pressure measuring device and a timing device. The Ringrose '405 patent discloses a method for measuring the viscosity of blood by placing a sample of it on a support and directing a beam of light through the sample and then detecting the reflected light while vibrating the support at a given frequency and amplitude. The Weber '632 patent discloses a method and apparatus for determining the fluidity of blood by drawing the blood through a capillary tube measuring cell into a reservoir and then returning the blood back through the tube at a constant flow velocity and with the pressure difference between the ends of the capillary tube being directly related to the blood viscosity. The Gunn '830 patent discloses an apparatus for determining blood viscosity that utilizes a transparent hollow tube, a needle at one end, a plunger at the other end for creating a vacuum to extract a predetermined amount and an apertured weight member that is movable within the tube and is movable by gravity at a rate that is a function of the viscosity of the blood. The Kiesewetter '239 patent discloses an apparatus for determining the flow shear stress of suspensions, principally blood, using a measuring chamber comprised of a passage configuration that simulates the natural microcirculation of capillary passages in a being. The Kiesewetter '821 patent discloses another apparatus for determining the viscosity of fluids, particularly blood, that includes the use of two parallel branches of a flow loop in combination with a flow rate measuring device for measuring the flow in one of the branches for determining the blood viscosity. The Kron '127 patent discloses an apparatus and method for determining blood viscosity of a blood sample over a wide range of shear rates. The Merrill '577 patent discloses an apparatus and method for determining the blood viscosity of a blood sample using a hollow column in fluid communication with a chamber containing a porous bed and means for measuring the blood flow rate within the column. The Hori '678 patent discloses a method for measurement of the viscosity change in blood by disposing a temperature sensor in the blood flow and stimulating the blood so as to cause a viscosity change. The Esvan '415 patent discloses an apparatus that detects the change in viscosity of a blood sample based on the relative slip of a drive element and a driven element, which holds the blood sample, that are rotated. The Taniguchi '529 patent discloses a method and apparatus for determining the viscosity of liquids, e.g., a blood sample, utilizing a pair of vertically-aligned tubes coupled together via fine tubes while using a pressure sensor to measure the change of an internal tube pressure with the passage of time and the change of flow rate of the blood. The Bedingham '328 patent discloses an intravascular blood parameter sensing system that uses a catheter and probe having a plurality of sensors (e.g., an $O_2$ sensor, $CO_2$ sensor, etc.) for measuring particular blood parameters in vivo. The Schlain '398 patent discloses a intra-vessel method and apparatus for detecting undesirable wall effect on blood parameter sensors and for moving such sensors to reduce or eliminate the wall effect. The Davis '440 patent discloses an apparatus for conducting a variety of assays that are responsive to a change in the viscosity of a sample fluid, e.g., blood.

Viscosity measuring methods and devices for fluids in general are well-known. See for example, U.S. Pat. No. : 1,810,992 (Dallwitz-Wegner); U.S. Pat. No. 2,343,061 (Irany); U.S. Pat. No. 2,696,734 (Brunstrum et al.); U.S. Pat. No. 2,700,891 (Shafer); U.S. Pat. No. 2,934,944 (Eolkin); U.S. Pat. No. 3,071,961 (Heigl et al.); U.S. Pat. No. 3,116,630 (Piros); U.S. Pat. No. 3,137,161 (Lewis et al.); U.S. Pat. No. 3,138,950 (Welty et al.); U.S. Pat. No. 3,277,694 (Cannon et al.); U.S. Pat. No. 3,286,511 (Harkness); U.S. Pat. No. 3,435,665 (Tzentis); U.S. Pat. No. 3,520,179 (Reed); U.S. Pat. No. 3,604,247 (Gramain et al.); U.S. Pat. No. 3,666,999 (Moreland, Jr. et al.); U.S. Pat. No. 3,680,362 (Geerdes et al.); U.S. Pat. No. 3,699,804 (Gassmann et al.); U.S. Pat. No. 3,713,328 (Aritomi); U.S. Pat. No. 3,782,173 (Van Vessem et al.); U.S. Pat. No. 3,864,962 (Stark et al.); U.S. Pat. No. 3,908,441 (Virloget); U.S. Pat. No. 3,952,577 (Hayes et al.); U.S. Pat. No. 3,990,295 (Renovanz et al.); U.S. Pat. No. 4,149,405 (Ringrose); U.S. Pat. No. 4,302,965 (Johnson et al.); U.S. Pat. No. 4,426,878 (Price et al.); U.S. Pat. No. 4,432,761 (Dawe); U.S. Pat. No. 4,616,503 (Plungis et al.); U.S. Pat. No. 4,637,250 (Irvine, Jr. et al.); U.S. Pat. No. 4,680,957 (Dodd); U.S. Pat. No. 4,680,958 (Ruelle et al.); U.S. Pat. No. 4,750,351 (Ball); U.S. Pat. No. 4,856,322 (Langrick et al.); U.S. Pat. No. 4,899,575 (Chu et al.); U.S. Pat. No. 5,142,899 (Park et al.); U.S. Pat. No. 5,222,497 (Ono); U.S. Pat. No. 5,224,375 (You et al.); U.S. Pat. No. 5,257,529 (Taniguchi et al.); U.S. Pat. No. 5,327,778 (Park); and U.S. Pat. No. 5,365,776 (Lehmann et al.).

The following U.S. patents disclose viscosity or flow measuring devices, or liquid level detecting devices using optical monitoring: U.S. Pat. No. 3,908,441 (Virloget); U.S. Pat. No. 5,099,698 (Kath, et. al.); U.S. Pat. No. 5,333,497 (Br nd Dag A. et al.). The Virloget '441 patent discloses a device for use in viscometer that detects the level of a liquid in a transparent tube using photodetection. The Kath '698 patent discloses an apparatus for optically scanning a rotameter flow gauge and determining the position of a float therein. The Br nd Dag A. '497 patent discloses a method and apparatus for continuous measurement of liquid flow velocity of two risers by a charge coupled device (CCD) sensor.

U.S. Pat. No. 5,421,328 (Bedingham) discloses an intravascular blood parameter sensing system.

A statutory invention registration, H93 (Matta et al.) discloses an apparatus and method for measuring elongational viscosity of a test fluid using a movie or video camera to monitor a drop of the fluid under test.

The following publications discuss red blood cell deformability and/or devices used for determining such: *Measurement of Human Red Blood Cell Deformability Using a Single Micropore on a Thin $Si_3N_4$ Film*, by Ogura et al, IEEE Transactions on Biomedical Engineering, Vol. 38, No. 8, August 1991; *the Pall BPF4 High Efficiency Leukocyte Removal Blood Processing Filter System*, Pall Biomedical Products Corporation, 1993.

A device called the "Hevimet 40" has recently been advertised at www.hevimet.freeserve.co.uk. The Hevimet 40 device is stated to be a whole blood and plasma viscometer that tracks the meniscus of a blood sample that falls due to gravity through a capillary. While the Hevimet 40 device may be generally suitable for some whole blood or blood plasma viscosity determinations, it appears to exhibit several significant drawbacks. For example, among other things, the Hevimet 40 device appears to require the use of anti-coagulants. Moreover, this device relies on the assumption that the circulatory characteristics of the blood sample are for a period of 3 hours the same as that for the patient's circulating blood. That assumption may not be completely valid.

Notwithstanding the existence of the foregoing technology, a need remains for an apparatus and method for obtaining the viscosity of the blood of a living being in-vivo and over a range of shears and for the provision of such data in a short time span.

OBJECTS OF THE INVENTION

Accordingly, it is the general object of the instant invention to provide an apparatus and methods for meeting that need.

It is a further object of this invention to provide viscosity measuring an apparatus and methods for determining the viscosity of circulating blood over a range of shear rates, especially at low shear rates.

It is still yet a further object of this invention to provide an apparatus and methods for determining viscosity of the circulating blood of a living being (e.g., in-vivo blood viscosity measurement) without the need to directly measure pressure, flow and volume.

It is yet another object of this invention to provide an indication of the viscosity of the circulating blood of a living being in a short span of time.

It is yet another object of this invention to provide an apparatus and methods for measuring the viscosity of the circulating blood of a living being and with minimal invasiveness.

It is still yet another object of the present invention to provide an apparatus and methods for measuring the viscosity of the circulating blood of a living being that does not require the use of anti-coagulants, or other chemicals or biologically active materials.

It is still yet even another object of the present invention to provide an apparatus and method for measuring the viscosity of blood of a living being that does not require the blood to be exposed to atmosphere or oxygen.

It is still yet another object of the present invention to provide an apparatus and method for determining the viscosity of the circulating blood contemporaneous with the diversion of the blood into a conveying means (e.g., needle) when that means is coupled to, e.g., inserted into, the patient.

It is still yet another object of the present invention to provide an apparatus and methods for measuring the circulating blood viscosity of a living being that comprises disposable portions for maintaining a sterile environment, ease of use and repeat testing.

It is still yet another object of the present invention to provide a blood viscosity measuring apparatus and methods for determining the thixotropic point of the blood.

It is even yet another object of the present invention to provide an apparatus and methods for determining the yield stress of the circulating blood.

It is moreover another object of the present invention to provide an apparatus and methods for detecting circulating blood viscosity to evaluate the efficacy of pharmaceuticals, etc., to alter blood viscosity of the circulating blood of a living being.

It is even yet another object of this invention to provide an apparatus and methods for detecting the viscosity of the circulating blood of a patient while negating the effects of venous pressure.

SUMMARY OF THE INVENTION

In accordance with one aspect of this invention an apparatus is provided for effecting the viscosity measurement (e.g., in real-time) of circulating blood in a living being. The apparatus comprises: a lumen arranged to be coupled to the vascular system of the being; a pair of tubes having respective first ends coupled to the lumen for receipt of circulating blood from the being, and wherein one of the pair of tubes comprises a capillary tube having some known parameters; a valve for controlling the flow of circulating blood from the being's vascular system to the pair of tubes; and an analyzer, coupled to the valve, for controlling the valve to permit the flow of blood into the pair of tubes whereupon the blood in each of the pair of tubes assumes a respective initial position with respect thereto. The analyzer is also arranged for operating the valve to isolate the pair of tubes from the being's vascular system and for coupling the pair of tubes together so that the position of the blood in the pair of tubes changes. The analyzer is also arranged for monitoring the blood position change in one of the tubes and detecting a single blood position in the other one of the pair of tubes and calculating the viscosity based thereon.

In accordance with another aspect of this invention a method is provided for determining the viscosity (e.g., in real-time) of circulating blood of a living being. The method comprises the steps of: (a) providing access to the circulating blood of the living being to establish an input flow of circulating blood; (b) dividing the input flow of circulating blood into a first flow path and a second flow path into which respective portions of the input flow pass and wherein one of the first or second flow paths includes a passageway portion having some known parameters; (c) isolating the first and second flow paths from the input flow and coupling the first and second flow paths together so that the position of the blood in each of the flow paths changes; (d) monitoring the blood position change in one of the first and second flow paths over time; (e) detecting as single blood position in the other one of said first and second flow paths; and (f) calculating the viscosity of the circulating blood based on the blood position change, the single blood position and on selected known parameters of the passageway portion.

In accordance with still another aspect of this invention an apparatus is provided for effecting the viscosity measurement (e.g., in real-time) of circulating blood in a living being. The apparatus comprises: a lumen arranged to be coupled to the vascular system of the being; a pair of tubes having respective first ends and second ends wherein the first ends are coupled together via a capillary tube having some known parameters; a valve for controlling the flow of circulating blood from the being's vascular system to the pair of tubes wherein the valve is coupled to a second end of one of the pair of tubes and is coupled to the lumen; and an analyzer, coupled to the valve, for controlling the valve to permit the flow of blood into the pair of tubes whereupon the blood in each of the pair of tubes assumes a respective initial position with respect thereto. The analyzer also is arranged for operating the valve to isolate the pair of tubes from the being's vascular system so that the position of the blood in the pair of tubes changes. The analyzer also is arranged for monitoring the blood position change in one of the tubes and detecting a single blood position in the other one of the pair of tubes and calculating the viscosity of the blood based thereon.

In accordance with yet another aspect of this invention a method is provided for determining the viscosity (e.g., in real-time) of circulating blood of a living being. The method comprises the steps of: (a) providing access to the circulating blood of the living being to form an input flow of circulating blood; (b) directing the input flow into one end of a pair of tubes coupled together via a passageway having some known parameters whereby the input flow passes through a first one of the pair of tubes, through the passageway and into a first portion of a second one of the pair of tubes in order to form respective columns in the first and second tubes; (c) isolating the respective columns from the input flow so that the position of the blood in each of the columns changes; (d) monitoring the blood position change in one of the columns of blood over time; (e) detecting a single blood position in the other one of the pair of tubes; and (f) calculating the viscosity of the circulating blood based on the blood position change, the single blood position and on selected known parameters of the passageway.

DESCRIPTION OF THE DRAWINGS

Other objects and many of the intended advantages of this invention will be readily appreciated when the same becomes better understood by reference to the following detailed description when considered in connection with the accompanying drawings wherein.

DETAILED DESCRIPTION OF THE PREFERRED EMBODIMENTS

Figure 1:
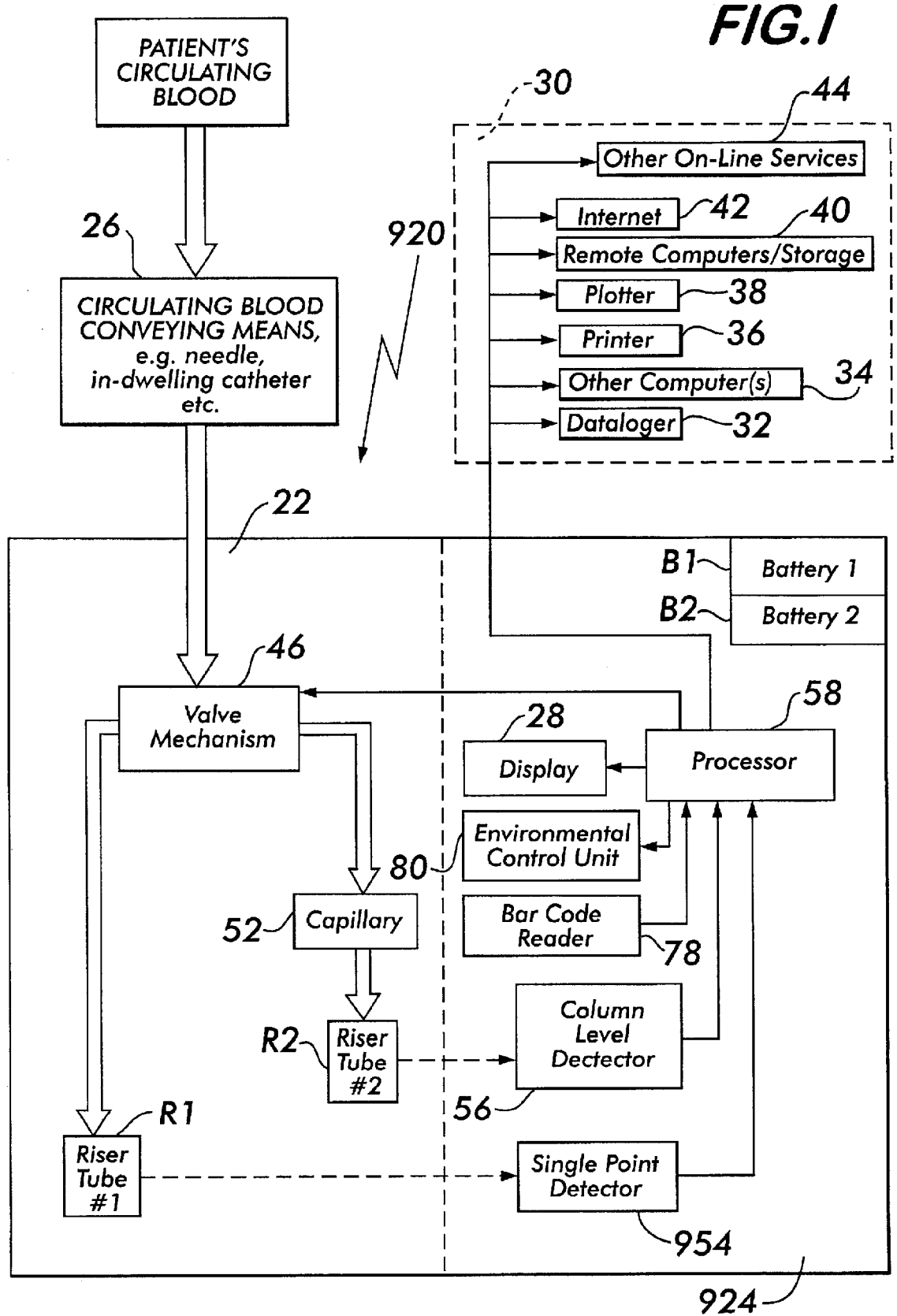
FIG. 1 is a block diagram of the dual riser/single capillary (DRSC) viscometer.

As stated previously, the present application is a Continuation-in-Part of Co-Pending application Ser. No. 09/439,795 (now U.S. Pat. No. 6,322,524), filed Nov. 12, 1999, entitled DUAL RISER/SINGLE CAPILLARY VISCOMETER, which in turn is a Continuation-in-Part of application Ser. No. 08/919,906 filed Aug. 28, 1997 (now U.S. Pat. No. 6,019,735), entitled VISCOSITY MEASURING APPARATUS AND METHOD OF USE, assigned to the same Assignee as the present invention and all of whose entire disclosures are incorporated by reference herein. For measuring the viscosity of circulating blood, including whole blood, of a living being, the apparatus and method as disclosed in U.S. Pat. No. 6,019,735 are generally preferable. To negate venous pressure effects at low shear rates, cuffing the living being, or other suitable means, may be used with that apparatus and method. of a living being, the apparatus and method as disclosed in U.S. Pat. No. 6,019,735 are An alternative apparatus and method of the present invention to negate pressure at low shear rates for measuring the viscosity of circulating blood, including whole blood, of a living being is shown generally at 920 in FIG. 1. The dual riser/single capillary (DRSC) viscometer 920 basically comprises a blood receiving means 22 and an analyzer/output portion 924. The analyzer/output portion 924 is similar to the analyzer output portion 24 of application Ser. No. 09/439,795 (now U.S. Pat. No. 6,322,524), except that one of the column level detectors, e.g., column level detector 54 for riser tube R1, is replaced with a single point detector 954, as will be discussed in detail later. Suffice it to say for now, that the apparatus 920 is similar in structure and operation to the apparatus 20 except for the substitution of one of the column level detectors with a single point detector 954.

The patient is coupled to the DRSC viscometer 920 through a circulating blood conveying means 26, e.g., a needle, an IV needle, an in-dwelling catheter, etc., or any equivalent structure that can convey circulating blood from a patient to the DRSC viscometer 20. As will be discussed in detail later, the analyzer/output portion 924 provides a display 28 for presenting the viscosity information, as well as other information to the operator. The analyzer/output portion 924 may also provide this information to other suitable output means 30, such as a datalogger 32, other computer(s) 34, a printer 36, a plotter 38, remote computers/storage 40, to the Internet 42 or to other on-line services 44.

The blood receiving means 22 basically comprises a valve mechanism 46 coupled to a first riser tube R1 on one side and coupled to a second riser tube R2 via a capillary tube 52 on the other side. The capillary tube 52 is of small uniform inside diameter, e.g., 60 mm-length, 0.8 mm inside diameter. When the circulating blood conveying means 26 (hereinafter the "CBCM 26") is coupled to the blood receiving means 22, the valve mechanism 46 controls the flow of blood into the receiving means 22, as will be discussed in detail later. Each of the riser tubes R1 and R2 are preferably the same dimensions (e.g., 12 inch long, 2 mm inside diameter).

It should be understood that the blood receiving means 22 may be disposable or non-disposable. As will be discussed in detail later, where the blood receiving means 22 are disposable, the components (valve mechanism 46, riser tubes R1 and R2 and capillary tube 52) are releasably secured in a blood receiving means housing that can be quickly and easily inserted, used during the viscosity test run and then quickly and easily removed for disposal; another disposable blood receiving means 22 is then inserted in preparation for the next viscosity test run. On the other hand, where the blood receiving means 22 is non-disposable, the components (valve mechanism 46, riser tubes R1 and R2 and capillary tube 52) can be thoroughly washed and cleaned in place in preparation for the next viscosity test run.

It should be understood that the capillary tube 52 does not necessarily have to be an elongated tube but may comprise a variety of configurations such as a coiled capillary tube.

As mentioned earlier, the analyzer/output portion 924 differs from the analyzer/output portion 24 of application Ser. No. 09/439,795 (now U.S. Pat. No. 6,322,524) in that the analyzer/output portion 924 comprises only a single column level detector 56 and a single point detector 954. This modification to the analyzer/output portion 24 of application Ser. No. 09/439,795 (now U.S. Pat. No. 6,322,524) is based on the symmetry of the column of blood height (i.e., $h_1(t)$ and $h_2(t)$) vs. time data (see FIG. 6). As long as one of the two columns of blood 82/84 is monitored, the height vs. time data for the other column of blood can be generated by using a single height point from that column. In the invention of the present application, it is only necessary to monitor the change in position of one of the columns of blood in either riser tube R1 or riser tube R2 and to detect only one point from the other column of blood. The preferred method/means is to monitor the rising column of blood 84 which occurs in riser tube R2 and to detect the initial viscosity test run level (i.e., $h_{1i}$, as will be discussed in detail later) of the column of blood 82 in riser tube R1. Thus, it is within the broadest scope of this invention to cover a monitor that monitors either one of the moving columns of blood but not both (as is disclosed in application Ser. No. 09/439,795, now U.S. Pat. No. 6,322,524) and a single point detector for detecting one point from the other moving column of blood.

In particular, the analyzer/output portion 924 basically comprises the single column level detector 56, the single point detector 954, a processor 58, the display 28, a bar code reader 78, an environmental control unit 80, and a first battery B1 and a second back-up battery B2. The column level detector 56 (comprising an LED (light emitting diode) array 64 and a CCD (charge coupled device) 66, as will be discussed in detail later) monitors the rising level of blood in the second riser tube R2; furthermore, the single point detector 954, may comprise (but is not limited to) an LED 964 and a photodetector 966, which detect a specific level of the column of blood, e.g., $h_{1i}$, as will also be discussed in detail later.

The processor 58 (e.g., a "386" microprocessor or greater, or any equivalent) is arranged to analyze the data from the detector 56 and calculate the blood viscosity therefrom, as will also be discussed in detail later. Furthermore, the processor 58 also controls the display 28 for providing the viscosity information and the other information to the operator as well as to the other output means 30. The processor 58 also controls the valve mechanism 46 based on the data from the detector 56, as will be discussed later. Battery B1 provides all of the requisite power to the analyzer/output portion 924, with battery B2 serving as a back-up power supply. The bar code reader 78 and the environmental control unit 80 will be described later.

Figure 2:
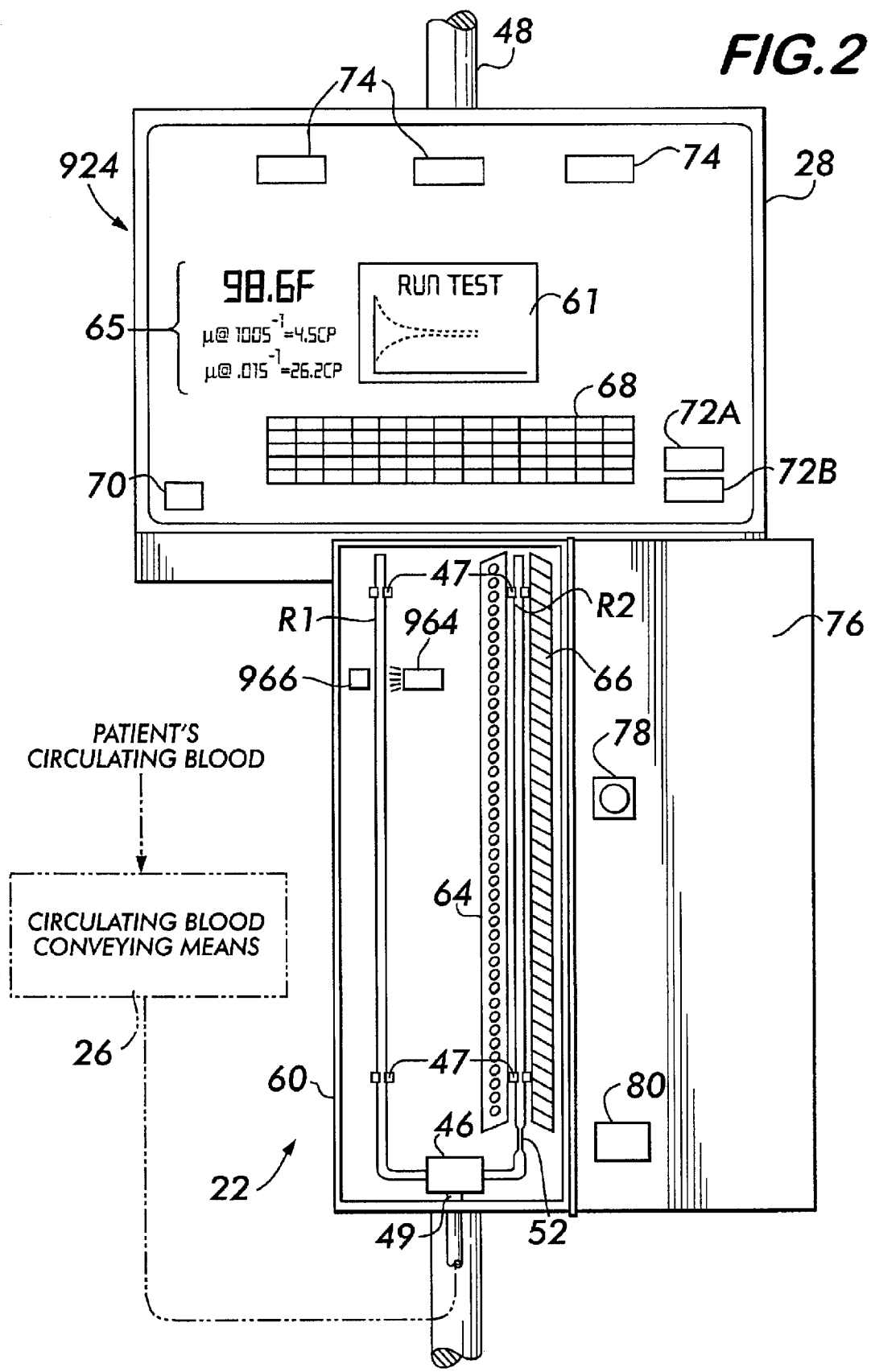
FIG. 2 is a front view of one embodiment of the DRSC viscometer depicting the respective housings for the blood receiving means, with its door opened, and the analyzer/output portion.
Figure 3:
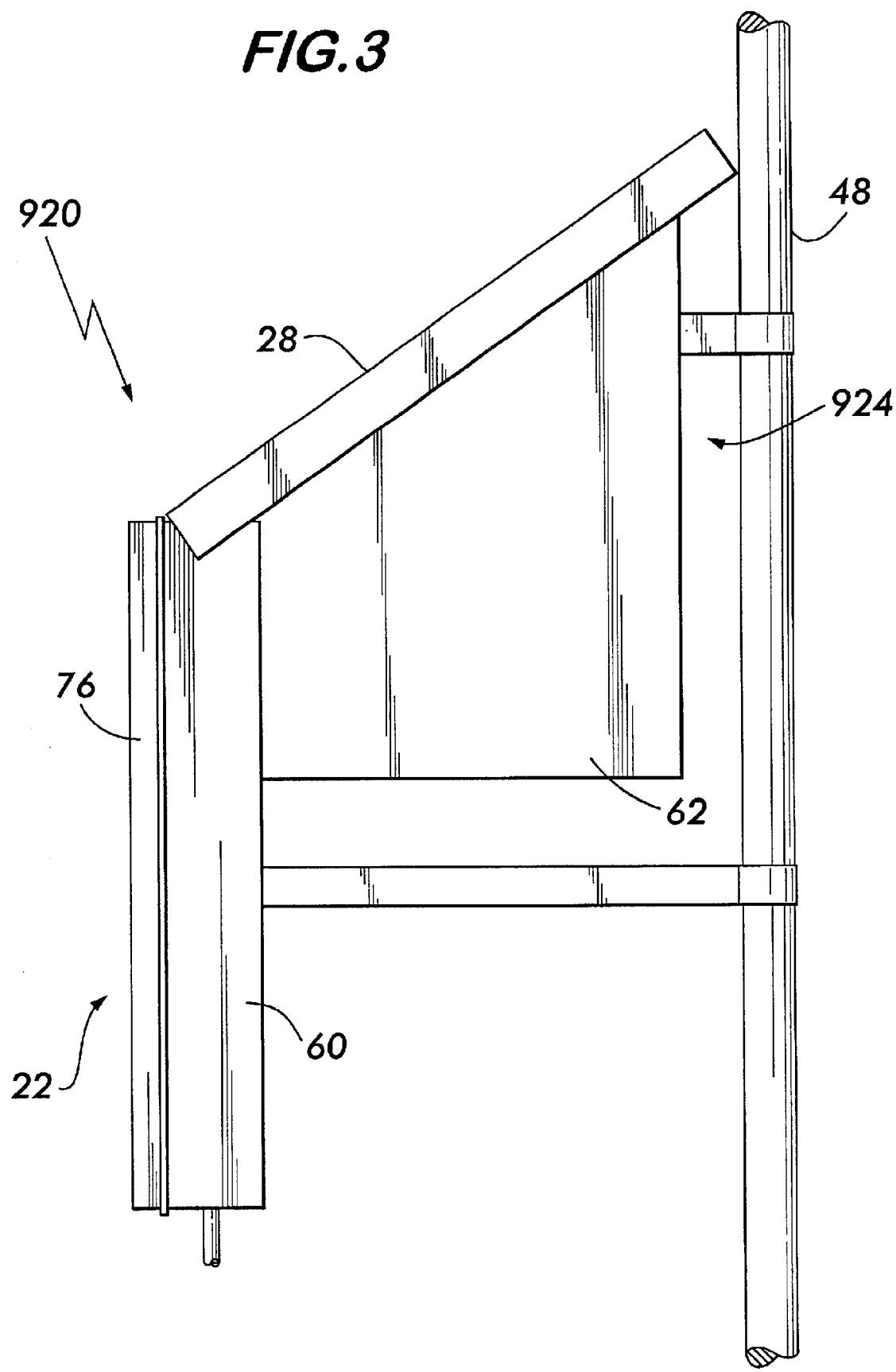
FIG. 3 is a side view of the embodiment of FIG. 2.

As shown more clearly in FIGS. 2–3, the DRSC viscometer 920 comprises the blood receiving means 22 and the analyzer/output portion 924 contained in respective housings 60 and 62, each of which can be releasably secured to a common frame, e.g., a conventional intravenous (IV) pole 48. In this configuration, the analyzer/output portion 924 can be positioned in an inclined orientation (see FIG. 3) to facilitate user operation and viewing of the display 28. However, it should be understood that the respective housing constructions are exemplary, and others can be incorporated without limiting the scope of this invention.

The display 28 may comprise any suitable conventional devices, e.g., an ELD (electroluminescent display) or LCD (liquid crystal display) that permits the visualization of both text and graphics. The resolution of this display 28 is preferably 800×600 VGA or above. Furthermore, while the preferred embodiment utilizes a touch screen display which incorporates, among other things:

graphical display 61
instruction, and/or data, display 65 (which also includes the command line display shown as "RUN TEST"; e.g., "TESTING", "TEST IN PROGRESS," etc.)
alphanumeric keypad 68
emergency stop button 70
battery status indicators, 72A and 72B
function buttons 74, it should be understood that any equivalent display device is within the broadest scope of the invention. Thus, any number of user interfaces and buttons may be available through the display 28. Therefore the invention 920 is not limited to the embodiment that is shown in FIG. 2. Moreover, the display 28 can be operated to minimize or maximize, or overlay any particular graphic or text screen, as is available in any conventional object-oriented operating system, such as Microsoft® WINDOWS.

The lower housing 60 comprises the blood receiving means 22 and the column level detector 56. In the preferred embodiment, the column level detector 56 comprises an LED (light emitting diode) array 64 and a CCD (charge coupled device) 66 located on opposite sides of the riser tube R2. When the column level detector 56 is operating, each LED array 64 illuminates the riser tube R2, and depending on whether there is fluid in the column, various pixels in the CCD 66 will either detect the light from the LED array 64 (no fluid in the column, thereby permitting the light to pass through the riser tube) or not (fluid is present and is blocking the passage of light from the LED array 64). The pixel data of each CCD 66 is passed to the analyzer/output 924 through conventional wire harnesses (not shown) for use by the processor 58. Furthermore, power for the LED arrays 64 and the CCDs 66 is provided via these wire harnesses from the batteries B1/B2, if the batteries are contained in the analyzer/output housing 62.

With respect to the single point detector 954, during operation of the apparatus 920, with the valve mechanism 46 open, blood flows up the riser tube R1 while the photodetector 966 continues to detect the light from the LED 964. Once the top of the column of blood 82 interrupts the light from the LED 964, the photodetector 966 informs the processor 58, which operates the valve mechanism 46, to halt any further blood flow into riser tube R1. This level of the column of blood defined as $h_{1i}$, forms the initial starting point of the column of blood in riser tube R1 for the viscosity test run, i.e., the column of blood in riser tube R1 falls away from this level $h_{1i}$ when the viscosity test begins. Since the position of the photodetector 966 is at the predetermined location, $h_{1i}$, above the reference level (FIG. 2), the photodetector 966 acts to verify that the initial position, $h_{1i}$ has been reached by the column of blood in riser tube R1.

Alternatively, as mentioned earlier, the column level detector 56 can be used to detect the falling column of blood in the first riser tube R1 and the single point detector 954 can be used to detect the initial viscosity test run position, $h_{2i}$, of the rising column of blood in riser tube R2. Thus, it is within the broadest scope of the invention to cover the use of one column level detector for monitoring the change in position of the blood column in one riser tube and the use of a single point detector for detecting a single point of the blood column in the other riser tube.

It should be understood that any one point of the blood column can be detected by the single point detector 954. The preferred point is the initial column level for the viscosity test run, namely $h_{1i}$ or $h_{2i}$. However, any other point in the column can be detected in order to generate the corresponding height vs. time data/curve.

Where the blood receiving means 22 is disposable, it is releasably secured in the housing 60 such that once a test run is completed and/or a new patient is to be tested, all of the lumens (e.g., the tube 50, the capillary 52, the riser tubes R1 an R2 and the valve mechanism 46) can be easily/quickly removed, disposed of and a new set inserted. For example, brackets 47 (FIG. 2) may be used to releasably secure the upper portions of the riser tubes R1 and R2 and the lower portions of the riser tubes R1 and R2; the valve mechanism 46 comprises a port 49 that fits snugly into an opening (not shown) in the bottom wall of the housing 60. The column level detector 56 is preferably not removable from the housing 60. A door 76 (which can be vertically or horizontally hinged to the housing 60) is provided to establish a darkened environment during the test run. The door 76 also supports the bar code reader 78, mentioned earlier. This bar code reader 78 automatically reads a bar code (not shown) that is provided on one of the riser tubes (e.g., R2). The bar code contains all of the predetermined data regarding the characteristics of the capillary tube 52 (e.g., its length and diameter) and the characteristics of the riser tubes R1 and R2. This information is passed to the processor 58 which is then used to determine the viscosity, as will be discussed in detail later. The bar code reader 78 passes this information to the processor 58 via the wire harnesses discussed earlier. It should be understood that the location (on the door 76) of the bar code reader 78 is exemplary only and that other locations within the unit are encompassed by the scope of the invention.

It should be understood that the brackets 47 do not interfere in any way with the column level monitoring, nor the single point detection, since the movement of blood in the riser tubes R1/R2 that is being monitored/detected during the viscosity test run is in between the upper and lower bracket 47 pairs.

The door 76 also supports an environmental control unit 80 (e.g., a heater, fan and/or thermostat) such that when it is closed in preparation for the test, the capillary tube 52 is then heated (or cooled) and maintained throughout the test run at the same temperature and environment as the patient. Prior to the run, the patient's temperature is taken and the operator enters this temperature (via the touch screen display 28). The environmental control unit 80 then operates to achieve and maintain this temperature. It should be noted that it is within the broadest scope of this invention to include a environmental control unit 80 that achieves and maintains the entire blood receiving means 22 at the patient's temperature during the run. Power to the bar code reader 78 and temperature control unit 80 is provided by the analyzer/output 924 through the wire harnesses (not shown) discussed previously.

Figure 11:
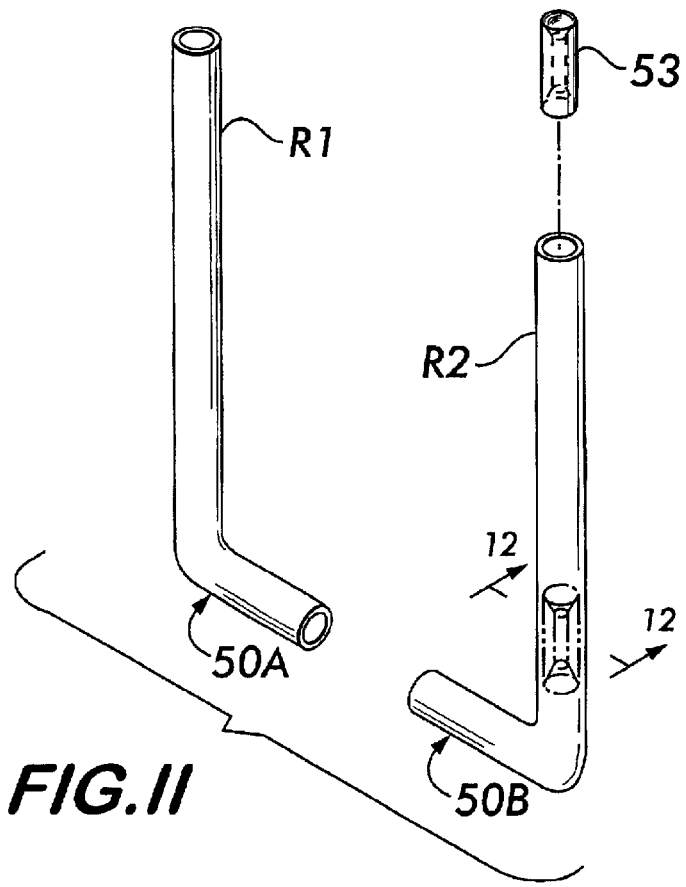
FIG. 11 depicts an implementation of the capillary and riser tube portion of the blood receiving means.
Figure 12:
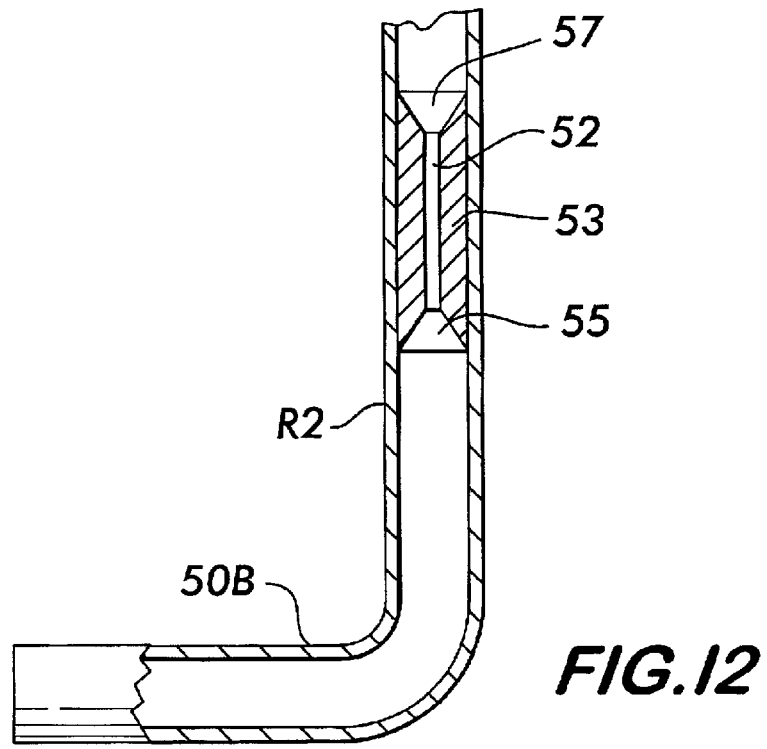
FIG. 12 is a partial cross-sectional view taken along line 12—12 of FIG. 11.

One exemplary implementation of the blood receiving means 22 is shown in FIGS. 11–12. In particular, the riser tubes R1 and R2 (e.g., injection-molded pieces) have integral elbows 50A and 50B that are inserted into respective ports (not shown) of the valve mechanism 46 (e.g., a single, 3-way stop cock valve). Prior to inserting the elbow portion 50B of riser R2 into its corresponding valve mechanism port, a capillary insert 53 having internal capillary 52, is positioned inside the riser tube R2. As shown most clearly in FIG. 12, the capillary insert 53 comprises a tapered entry port 55 and a tapered exit port 57 to minimize any turbulence as the circulating blood passes from the valve mechanism through the elbow 50B and up into riser tube R2.

The batteries B1/B2 may comprise a 12VDC, 4 amp-hour batteries, or any equivalent power supply (e.g., batteries used in conventional lap-top computers such as lithium ion batteries). The display 28 provides the status indicators 72A/72B for each battery in the DRSC viscometer 20. In particular, when the DRSC viscometer 20 is operating off of battery B1, the two battery indicators 72A/72B appear on the display 28. However, once battery B1 is depleted, the battery B1 indicator 72A disappears and the battery B2 indicator 72B blinks to warn the operator that the DRSC viscometer 20 is now operating off of the back-up battery B2 and re-charge of battery B1 is necessary.

Figure 4:
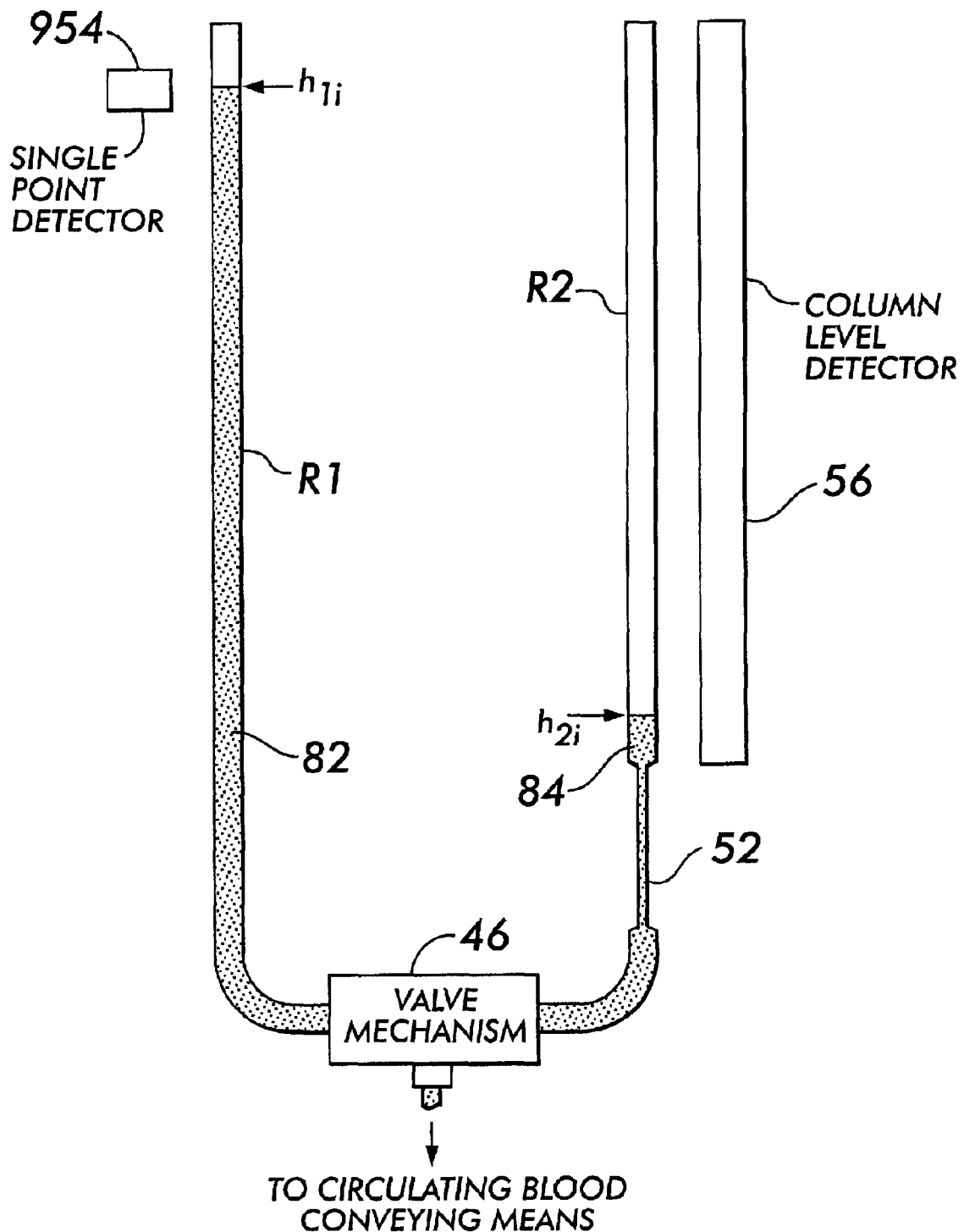
FIG. 4 is a functional diagram of the DRSC viscometer just prior to making a viscosity test run.

The concept of viscosity determination using the DRSC viscometer 920 is to monitor the change in height of one of two, oppositely-moving, columns of blood from the circulating blood of a patient and given the dimensions of a capillary through which one of the columns of blood must flow. The DRSC viscometer 920 accomplishes this by operating the valve mechanism 46 to first establish an optimum separation distance between the two columns of blood 82 and 84 in the respective riser tubes R1 and R2 (FIG. 4). Once established, the DRSC viscometer 20, via its valve mechanism 46, couples these two columns of blood 82/84 together and permits them to reach equilibrium while monitoring the movement of the two columns blood 82/84 (FIG. 5).

In particular, as shown in FIG. 4, continuous blood flow from the patient is permitted to flow from the CBCM 26, through the valve mechanism 46, and into both riser tubes R1 and R2. During this flow, the column level detector 56 monitors the height of the rising column of blood. When the optimum separation distance is achieved, i.e., when the column of blood in riser tube R1 reaches $h_{1i}$ and the column of blood in riser tube R2 reaches $h_{2i}$, the valve mechanism 46 stops the flow of blood from the CBCM 26 and simultaneously couples the columns of blood together (FIG. 5). As a result, the column of blood in riser R1 falls and the column of blood in riser R2 climbs toward a final equilibrium value, $h_\infty$ (which, as will be discussed later, is actually an offset known as "$\Delta h$"). It is the detection of one (preferably the rising column in riser tube R2) of these oppositely moving columns of blood (FIG. 5), which is important for blood viscosity determination, as will be discussed later. The graphical representation of $h_1(t)$ and $h_2(t)$ is shown in FIG. 6.

It should be understood that the optimum separation distance, i.e., $h_{1i}-h_{2i}$, as well as the dimensions of the capillary tube 52, avoids any oscillations of the columns of blood at the end of the viscosity test run. In other words, these two factors provide for the flat appearance of each of the plots $h_1(t)$ and $h_2(t)$ at the end of the viscosity test run, as shown in FIG. 6.

Figure 5:
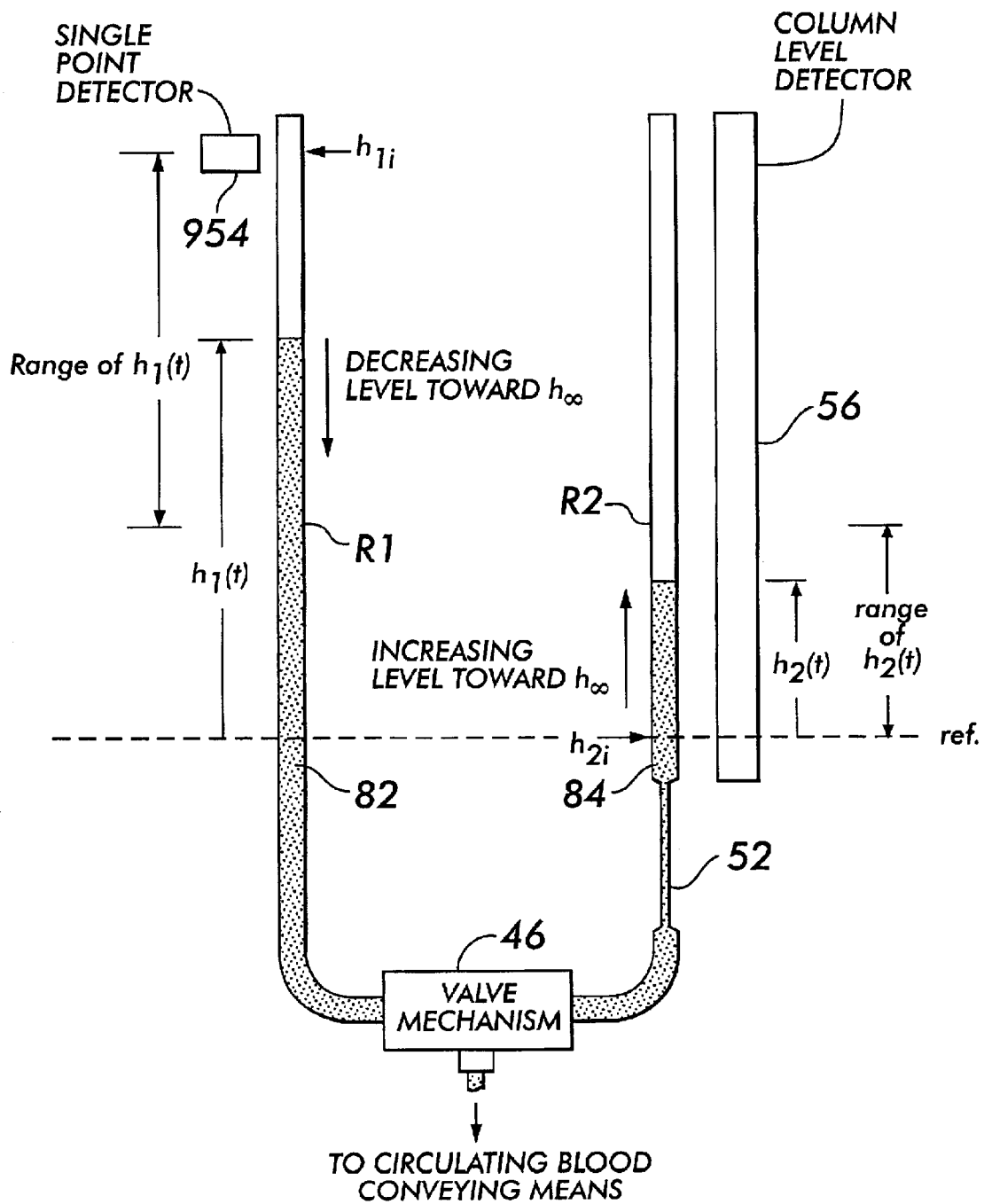
FIG. 5 is a functional diagram of the DRSC viscometer during the viscosity test run.
Figure 6:
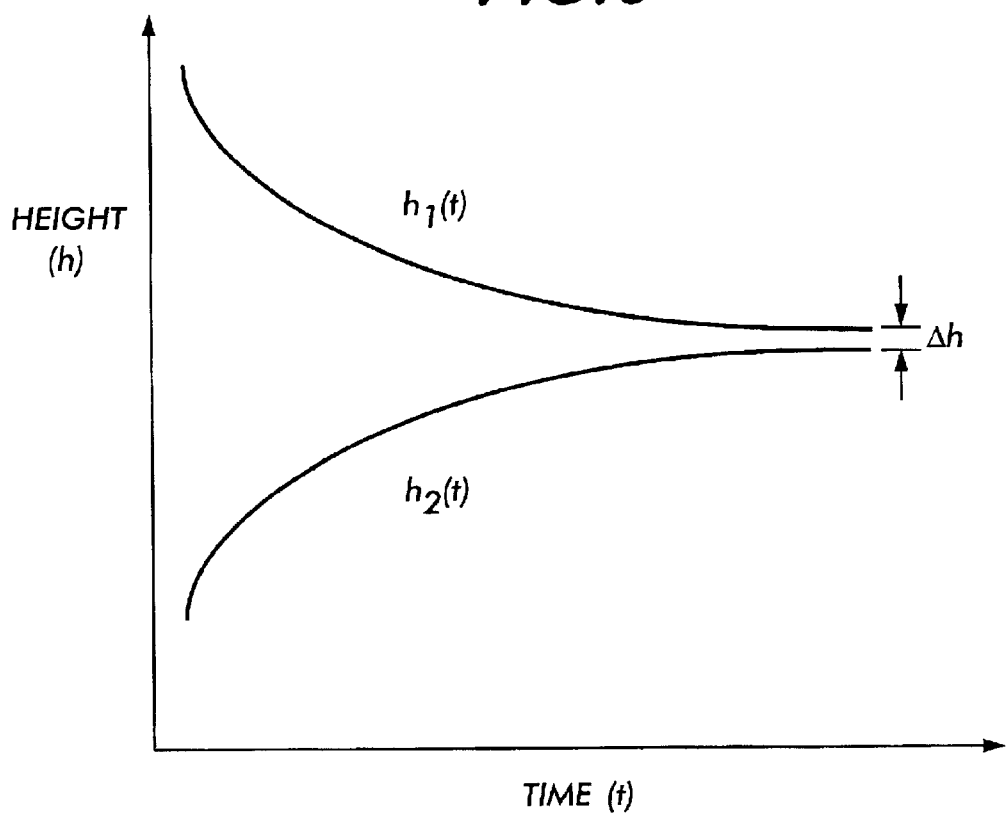
FIG. 6 depicts a graphical representation of the respective columns of fluid in the riser tubes of the DRSC viscometer during the viscosity test run.
Figure 7A:
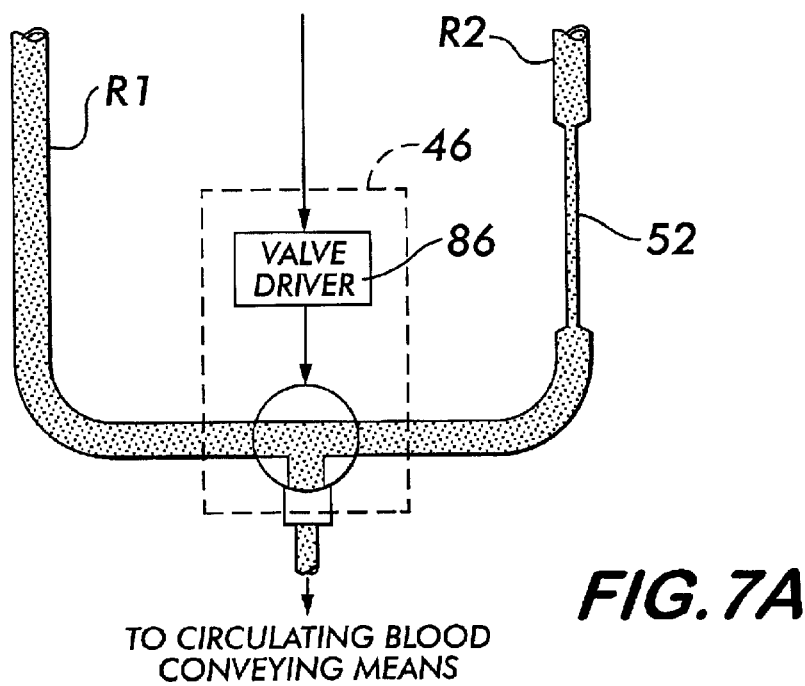
FIGS. 7A–7C depict the operation of the valve mechanism of the DRSC viscometer just prior to, and during, the viscosity test run.
Figure 7B:
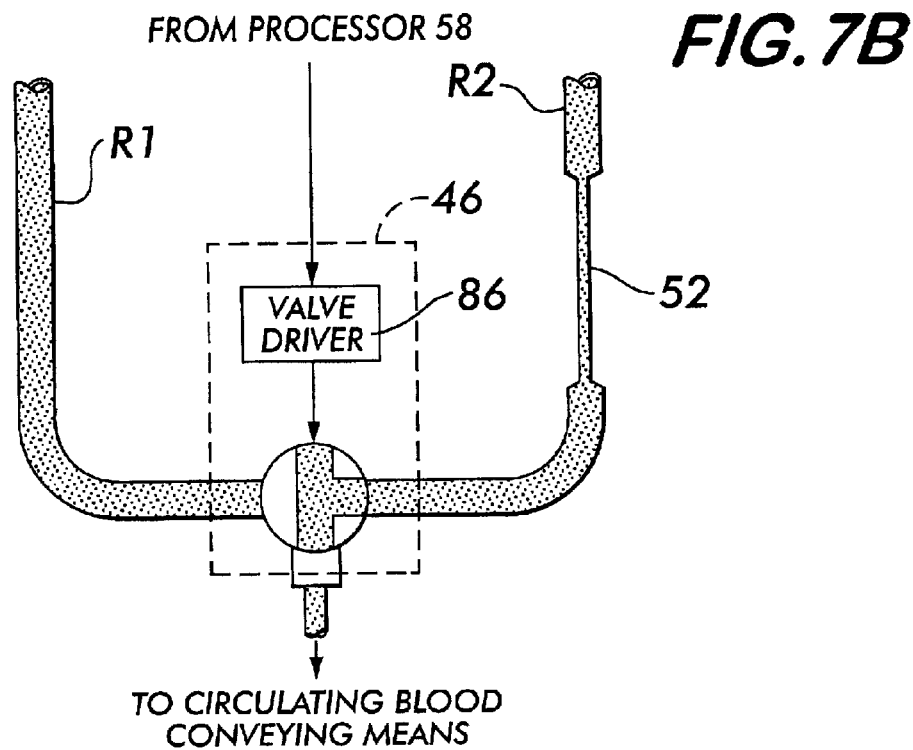
Figure 7C:
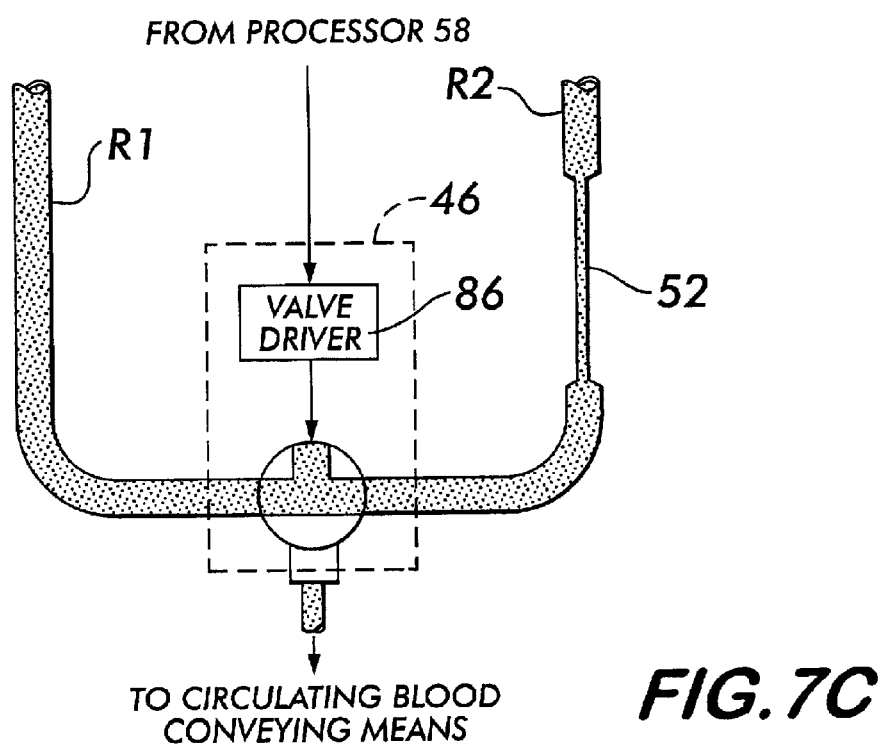

FIGS. 7A–7C depict a typical sequence of how the valve mechanism 46 establishes the pre-test run columns of blood (FIG. 4) and the test run columns of blood (FIG. 5). The valve mechanism 46 comprises a single, 3-way stop cock valve. The valve may comprise a solenoid (e.g., 500 mA solenoid, or stepper motor, etc., indicated by valve driver 86) that is pulsed by the processor 58 to operate the valve in the appropriate direction. In particular, the processor 58 commands rotation of the valve by issuing a positive or negative pulse to the solenoid. For example, to receive patient circulating blood flow into the DRSC viscometer 920 initially, the valve driver 86 configures the valve to allow circulating blood to enter both riser tubes R1 and R2 through respective tubing 13 and 14 (FIG. 7A). The column level detector 56 is monitoring the rising column of blood 84 during this time. Should the column of blood pre-test level $h_{1i}$ be reached first, the processor 58 issues a positive pulse to the valve driver 86 to close off flow to riser tube R1 (FIG. 7B); alternatively, should the column of blood pre-test level $h_{2i}$ be reached first, the processor 58 issues a negative pulse to close off flow to riser tube R2 while continuing to allow circulating blood flow into riser tube R1 (not shown). Finally, to couple the two riser tubes R1 and R2 together while isolating them from the circulating blood flow of the patient, the processor 58 commands the valve driver 86 to the position shown in FIG. 7C.

Figure 8:
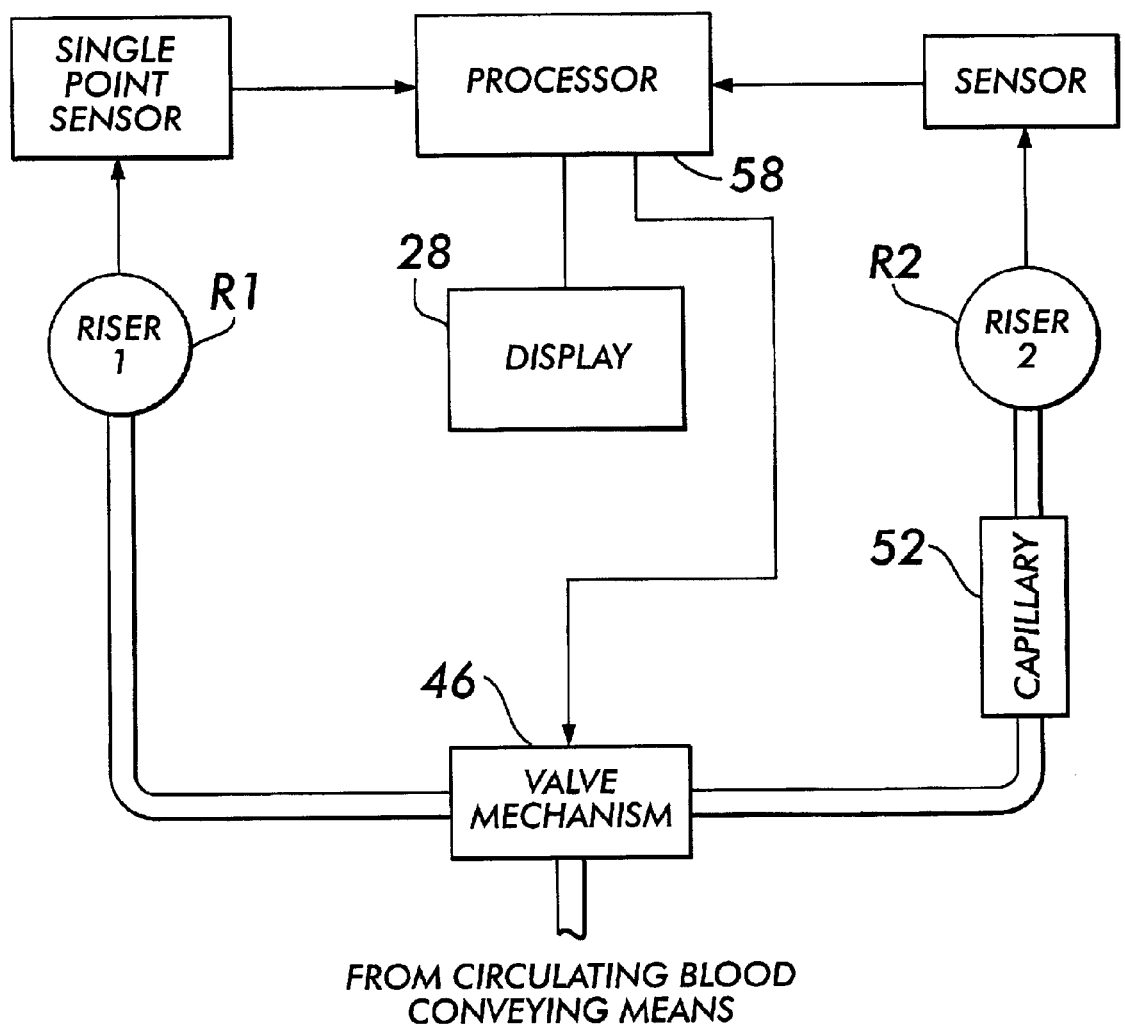
FIG. 8 is a block diagram for the DRSC viscometer which detects movement of the column of fluid in either of the riser tubes using various types of sensors.

As shown in FIG. 8, it is within the broadest scope of the invention to include any means and/or method for monitoring the movement of either one of the columns of blood

82/84 in the riser tubes R1/R2 and for detecting the single point in the other one of the columns and, as such, are not limited to the LED array 64/CCD 66 arrangement for the column level detector 56, nor to the LED 964/photodetector 966 arrangement for the single point detector 954. In fact, the following type of physical detections (indicated by "SENSOR" in FIG. 8) are covered by the present invention:

- d(Weight)/dt: the change in weight of either column of fluid with respect to time using a weight detecting means for either column of fluid as the sensor; e.g., $w_1(t)-w_2(t)$;
- d(Pressure)/dt: the change in pressure of either column of fluid with respect to time using a pressure transducer located at the top of either column of fluid; e.g., $p_1(t)-p_2(t)$;
- time of flight: the length of time it takes an acoustic signal to be emitted from a sensor (e.g., ultrasonic) located above either column of fluid and to be reflected and return to the sensor; e.g., time of flight$_1$(t)–time of flight$_2$(t);
- d(Volume)/dt: the change in volume of either column of fluid with respect to time; e.g., $V_1(t)-V_2(t)$;
- d(Position)/dt: the change in position of either column level using a digital video camera; e.g., $Pos_1(t)-Pos_2(t)$;
- d(Mass)/dt: the change in mass with respect to time for either column of fluid; e.g., $m_1(t)-m_2(t)$.

Figure 9A:
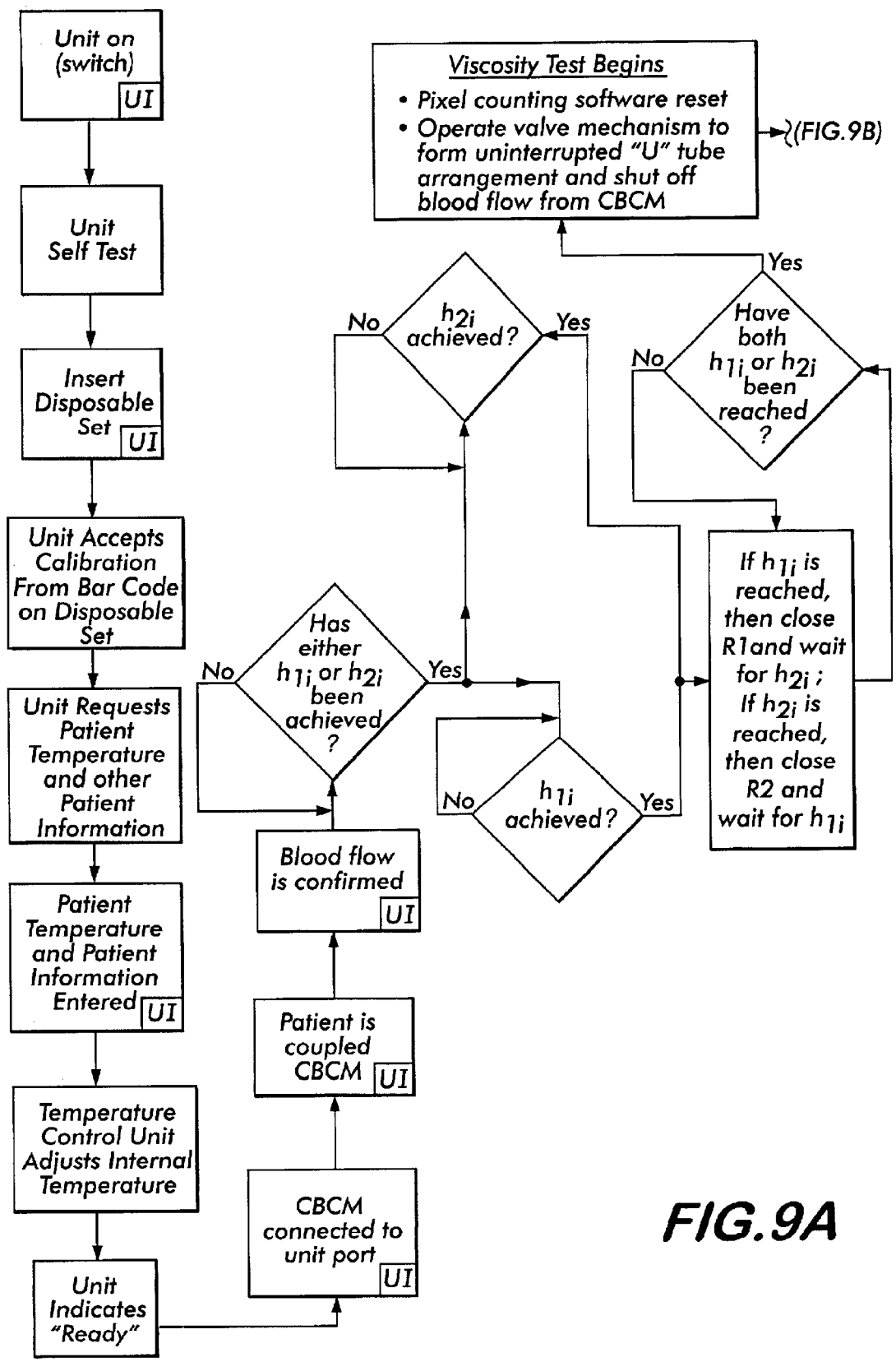
FIGS. 9A–9B comprise a flow chart of the operation of the DRSC viscometer.
Figure 9B:
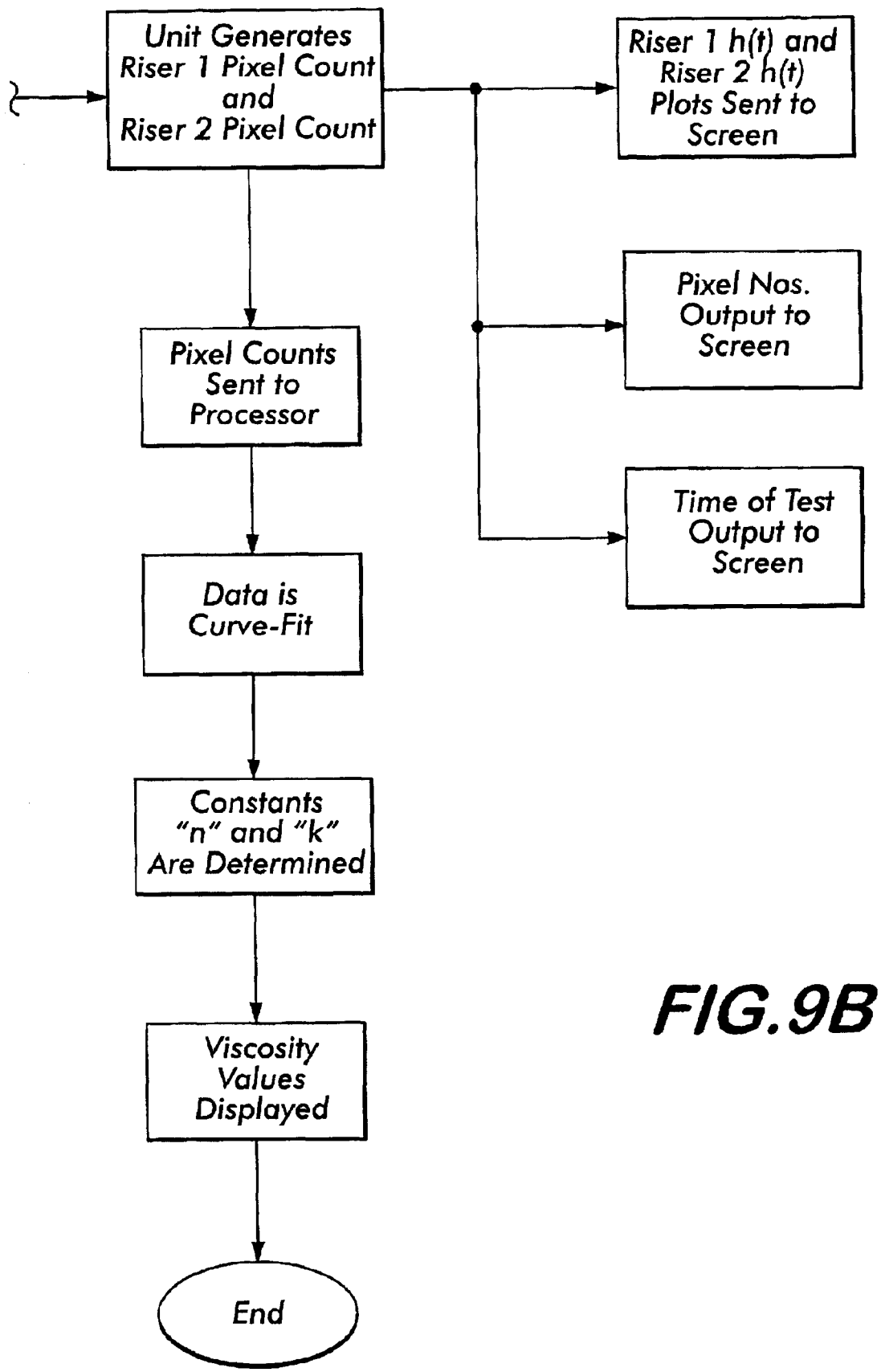

FIGS. 9A–9B comprise a flowchart of the detailed operation of the DRSC viscometer 920 to determine the viscosity of a patient's circulating blood flow. The overall time of the test run is approximately 3 minutes with the CCD 66. When the pixel values of the CCD 66 are no longer changing, the DRSC 20 determines that Δh has been reached and the test run is terminated.

As discussed earlier, the concept of viscosity determination using the DRSC viscometer 920 is to monitor the change in height of one of two, oppositely-moving, columns of blood from the circulating blood of a patient, along with detecting a single point from the other one of the two columns, and given the dimensions of a capillary through which one of the columns of blood must flow.

As stated in application Ser. No. 09/439,795 (now U.S. Pat. No. 6,322,524), there are a plurality of mathematical models that can be used as curve fitting models for the data obtained from the viscometers 920 and 1020, such as a power law model, a Casson model, a Carreau model, a Herschel-Bulkley model, a Powell-Eyring model, a Cross model, Carreau-Yasuda model. It is within the broadest scope of this invention to include all of these models. The following discussion utilizes a power law model and is used by way of example only and not by way of limitation. Thus, one skilled in the art could substitute any of the above curve fitting models for the exemplary power law model discussed below.

In particular, for non-Newtonian fluids, as is blood, the viscosity varies with shear rate, however, Hagen-Poiseuille flow within the capillary still holds for steady or quasi-steady laminar flow. For a fluid that is well-correlated with a non-Newtonian power law viscosity model, the capillary pressure drop and flow rate are related as follows:

$$\Delta P_c = \frac{4kL_c|\dot{\gamma}|^n}{\phi_c} = \frac{4kL_c}{\phi_c}\left|\left(\frac{3n+1}{n}\right)8\frac{Q}{\pi\phi_c^3}\right|^n \quad (1)$$

where the shear rate, $\dot{\gamma}$ is related to the capillary flow rate by:

$$\dot{\gamma} = \left(\frac{3n+1}{n}\right)8\frac{Q}{\pi\phi_c^3} \quad (2)$$

where the power law viscosity is defined as:

$$\mu = k|\dot{\gamma}|^{n-1} \quad (3)$$

and where $\Delta P_c$=capillary tube pressure drop (Pa)
$L_c$=length of capillary tube (m)
Q=volumetric flow rate (m$^3$/s)
k=consistency index (a constant used in capillary viscometry)—that is determined;
n=power law index (another constant used in capillary viscometry)—that is determined;
$\phi_c$=capillary tube diameter (m)
$\mu$=fluid viscosity (centipoise, CP)
$\dot{\gamma}$=shear rate (s$^{-1}$)

Since blood, a non-Newtonian fluid, is well-characterized with a power law viscosity model, Equation (1) can be re-written as:

$$\rho g(h_1 - h_2) = \frac{4kL_c}{\phi_c}\left\{2\left(\frac{3n+1}{n}\right)\cdot\left(\frac{\phi_r^2}{\phi_c^3}\right)\left(\frac{dh}{dt}\right)\right\}^n + \Delta h\rho g \quad (4)$$

where $\rho$=blood fluid density;
g=gravitational constant;
$h_1$=instantaneous height of the column of blood in riser R1
$h_2$=instantaneous height of the column of blood in riser R2
$\phi_c$=inside diameter of the capillary tube
$\phi_r$=inside diameter of riser tube and where $\phi_c \lll \phi_r$
Δh=an offset due to yield stress of the blood and is a property of blood.

It should be noted that the length of the capillary tube $L_c$ is assumed large such that any friction forces in the riser tubes R1 and R2 and connecting fluid components can be ignored. In addition, the diameter of the riser tubes R1 and R2 are equal.

By integrating both sides of Equation (4) with respect to time, the need to determine dh/dt is eliminated, which yields:

$$h_1 - h_2 - \Delta h = -\left\{\left(\frac{n-1}{n}\right)\alpha t + (\Delta h - h_0)^{\frac{n-1}{n}}\right\}^{\frac{n}{n-1}} \quad (5)$$

where
$h_0 = h_1(t) - h_2(t)$ at t=0; i.e., $h_0 = h_{1i} - h_{2i}$; and $$\alpha = -\frac{1}{2}\left(\frac{4kL_c}{\rho g\phi_c}\right)^n\left(\frac{n}{3n+1}\right)\left(\frac{\phi_c^3}{\phi_r^2}\right) \quad (6)$$

In order to determine the viscosity, it is necessary to determine the values for k and n using curve fitting based on the test run data. In particular, the following procedure is used:

1) Conduct a test run and obtain all $h_1(t)$ and $h_2(t)$ data;
2) Fit curves through the data to obtain symbolic expressions for $h_1(t)$ and $h_2(t)$;

3) Determine all $h_1(t)$–$h_2(t)$ data, as well as $\Delta h$;
3) Assume values for the power law parameters k and n;
4) Calculate the following error values for all data points:

$$\text{Error} = \left| (h_1 - h_2 - \Delta h) - \left\{ \left( \frac{n-1}{n} \right) \alpha t + (\Delta h - h_0)^{\frac{n-1}{n}} \right\}^{\frac{n}{n-1}} \right| \quad (7)$$

Figure 10A:
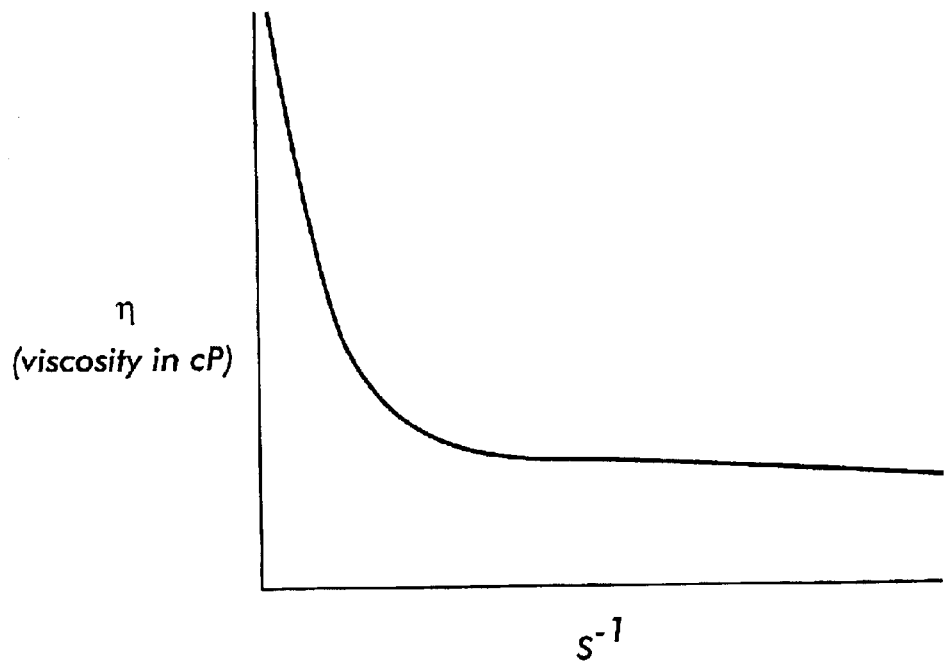
FIG. 10A depicts a graphical representation of the viscosity of a living patient's circulating blood plotted for a range of shear rates.
Figure 10B:
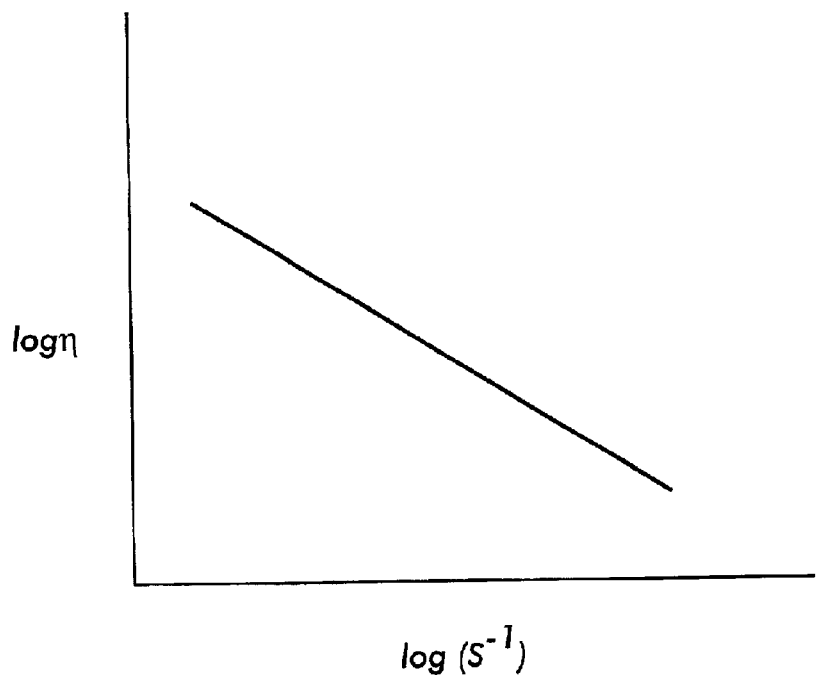
FIG. 10B depicts a graphical representation of the logarithm of the viscosity of a living patient's circulating blood plotted against the logarithm of shear rates.

6) Sum the error values for all data points;
7) Iterate to determine the values of k and n that minimize the error sum; and
8) Use the determined k and n values in Equations (2) and (3) to calculate viscosity. FIG. 10A depicts a graphical representation of the viscosity of the patient's circulating blood versus a range of shear rates and FIG. 10B depicts a logarithmic depiction of viscosity versus shear rate. It should be understood that the curves depicted in those graphs are identical mathematically and that the DRSC viscometer 920 disclosed above ensures greater accuracy than existing technology.

A combined handle/filter assembly (not shown) could be used at the top of the riser tubes R1 and R2. This assembly permits the introduction of an inert gas at atmospheric pressure into the riser tubes R1 and R2 above the respective column of fluids. In addition, this assembly acts as a handle for the insertion and removal of the blood receiving means 22 when a disposable blood receiving means 22 is utilized.

It should also be understood that the locations of many of the components in the blood receiving means 22 are shown by way of example only and not by way of limitation. For example, the capillary 52 can be positioned horizontally or vertically; the valve mechanism 46 does not necessarily have to be located at the elbow portions 50A/50B of the riser tubes R1 and R2. It is within the broadest scope of the invention to include various locations of the components within the blood receiving means 22 without deviating from the invention. In fact, the next embodiment discussed below utilizes such various locations.

In FIGS. 13–21, there is shown a more preferred embodiment 1020 of the DRSC viscometer described heretofore. This second embodiment 1020 for all intents and purposes is the same as the first embodiment 920 except for the location of the valve mechanism 46, the use of a vacutainer mechanism 101, the position of the capillary tube 52 and the requisite volume of blood that is used in the blood receiving means. As a result, the equations (i.e., Equations 1–7) governing the operation of this second embodiment 1020 and the plots concerning the column levels'time response and viscosity (i.e., FIGS. 6, 10A and 10B) are similar and will not be repeated here. Thus, the common details of the construction and operation of embodiment 1020 will not be reiterated. Furthermore, as stated previously with respect to the embodiment 920, the capillary tube 52 used in the embodiment 1020 does not necessarily have to be an elongated tube but may comprise a variety of configurations such as a coiled capillary tube.

Figure 13:
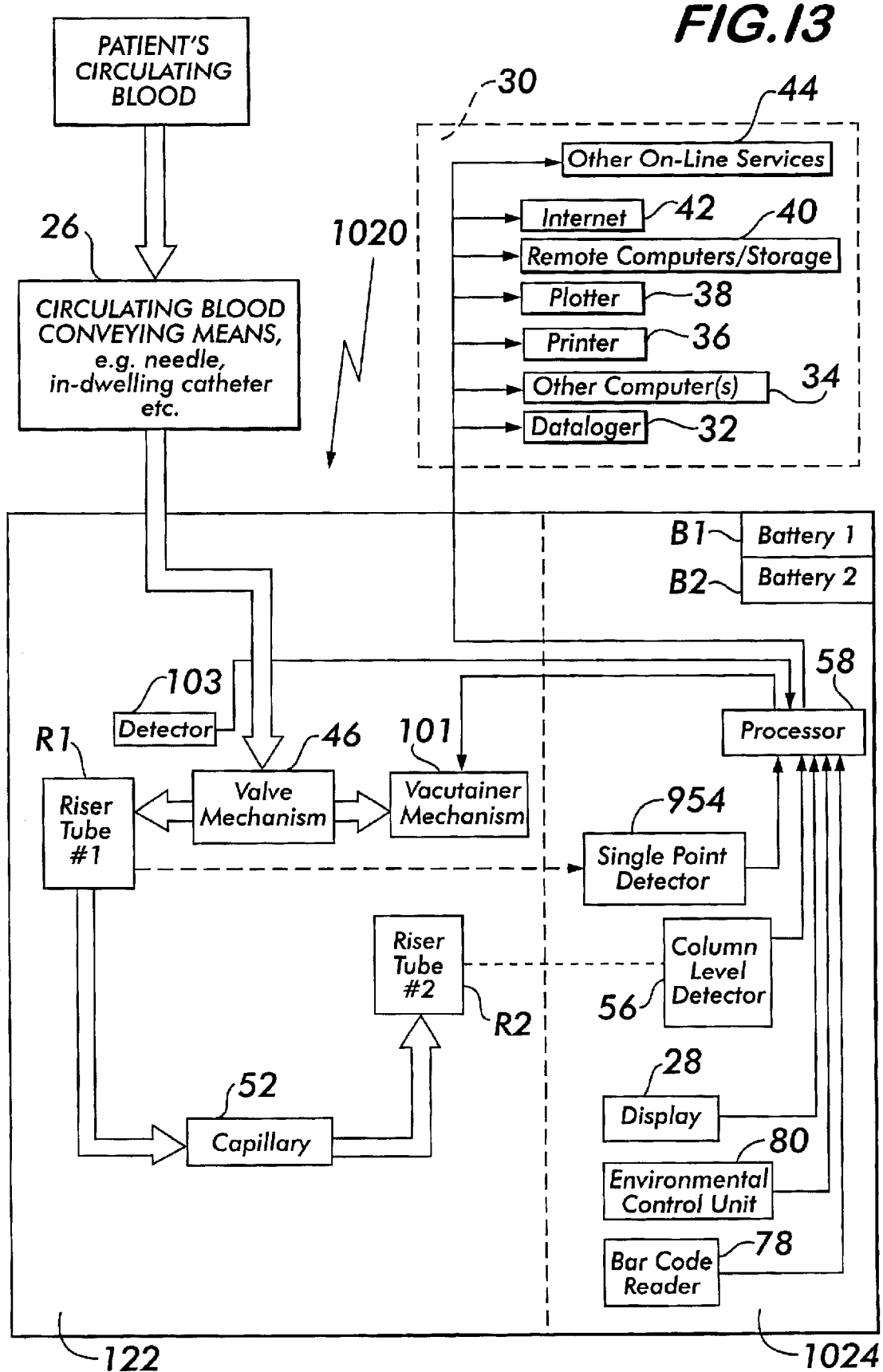
FIG. 13 is a block diagram of a second more preferred dual riser/single capillary (DRSC) viscometer.
Figure 14:
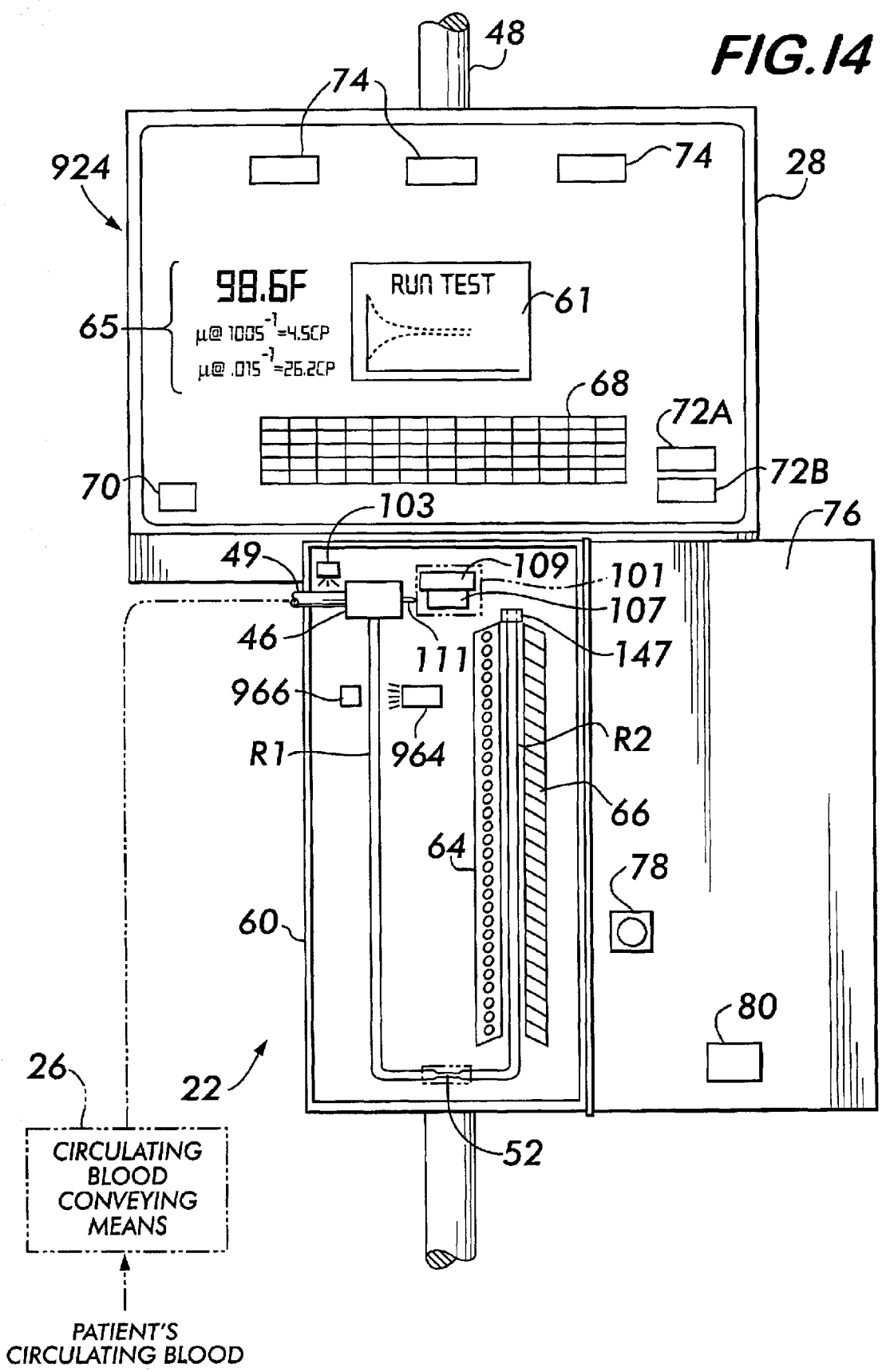
FIG. 14 is a front view of the second embodiment of the DRSC viscometer depicting the respective housings for the blood receiving means, with its door opened, and the analyzer/output portion.
Figure 15:
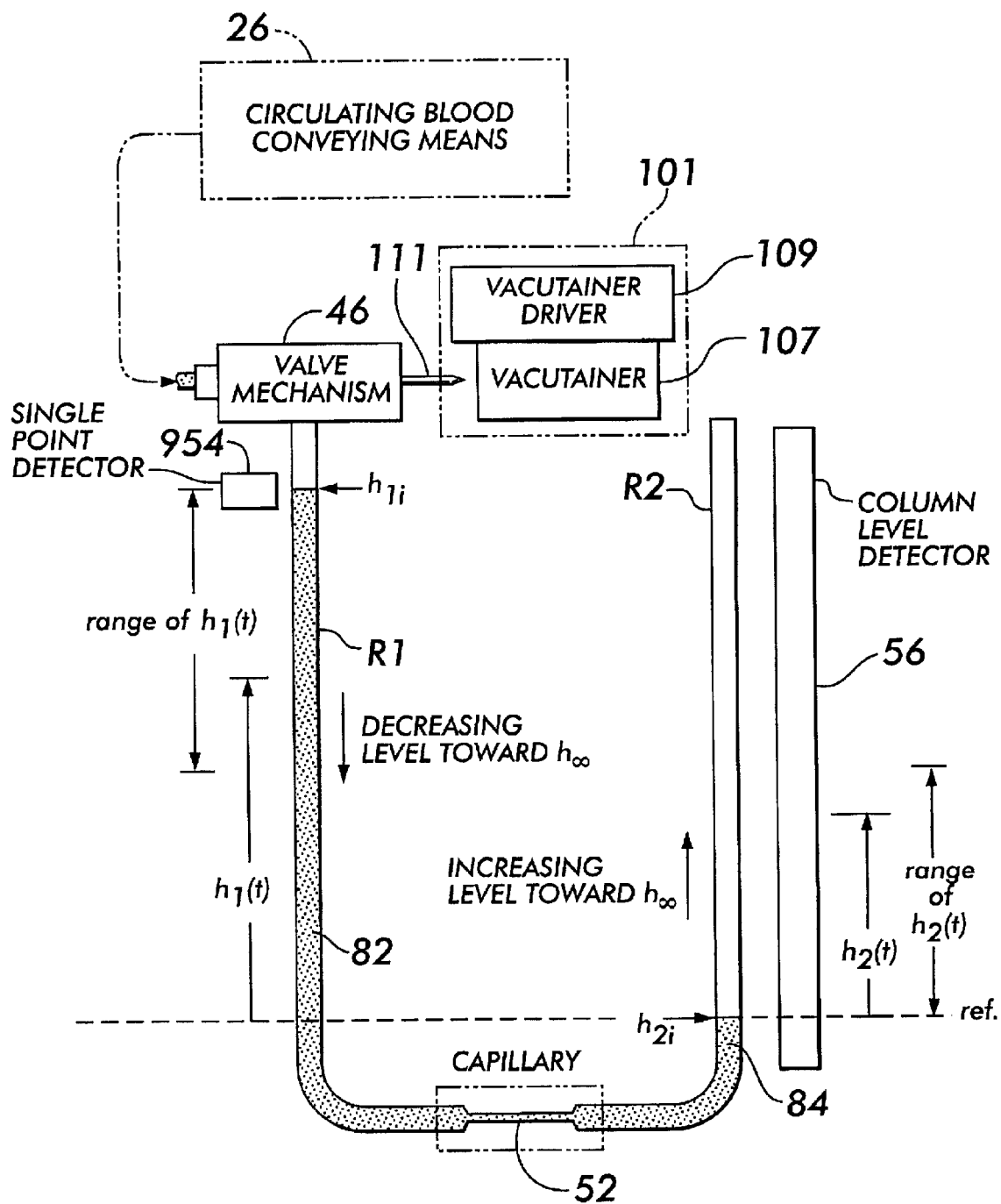
FIG. 15 is a functional diagram of the second embodiment of the DRSC viscometer just prior to making a viscosity test run.
Figure 16:
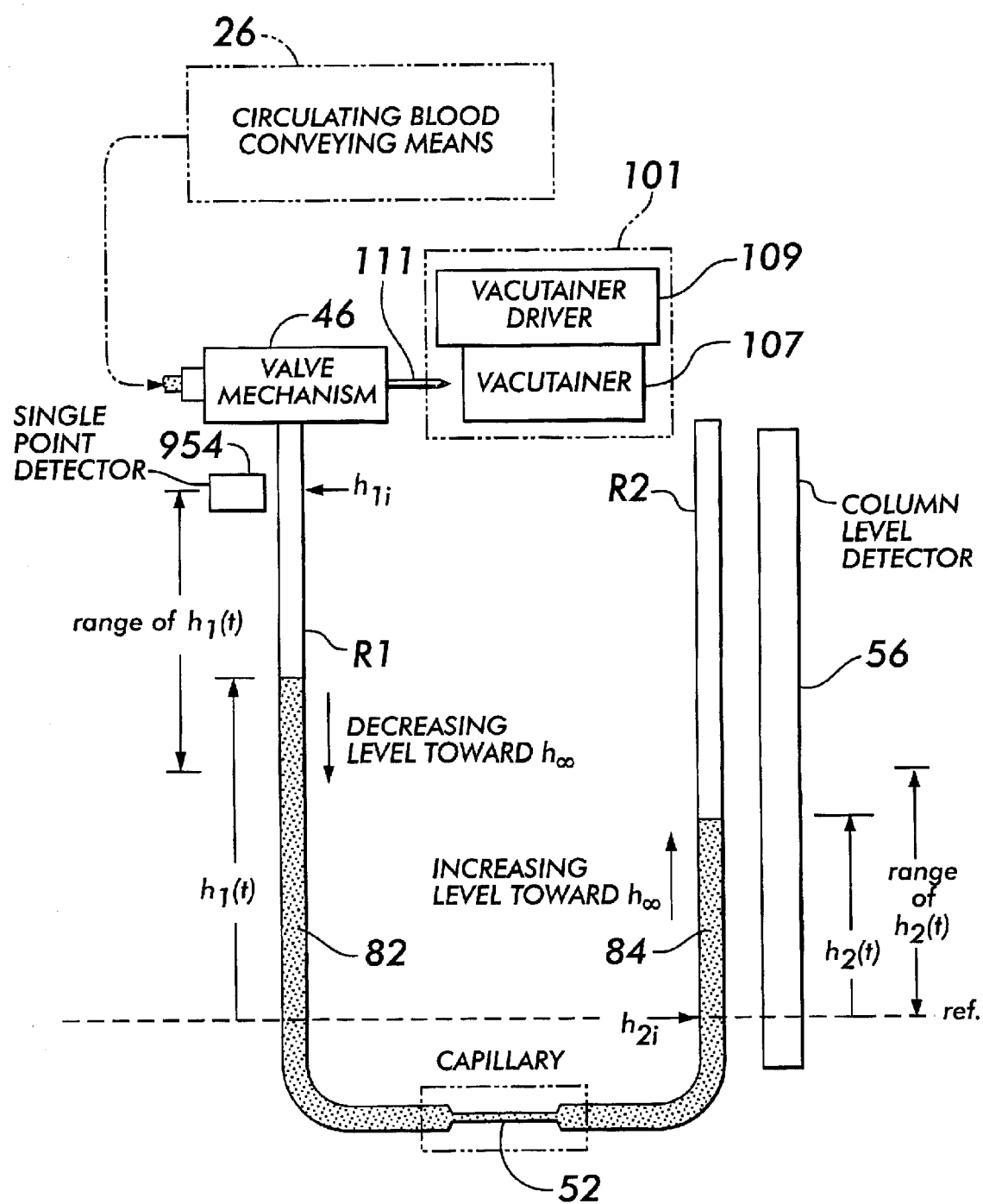
FIG. 16 is a functional diagram of the second embodiment of the DRSC viscometer during the viscosity test run.

As can be seen in FIG. 13, the embodiment 1020 comprises a blood receiving means 122 and the analyzer/output portion 1024. As with the blood receiving means 22 described earlier, the blood receiving means 122 can be disposable or re-usable. As an example of a disposable blood receiving means 122, a friction-type fitting 147 (see FIG. 14) releasably secures the top end of riser tube R2 into the housing 60 while the valve mechanism 46 is friction-fitted at the top of the riser tube R1 into the housing 60. Thus, to remove the disposable blood receiving means 122, the operator need only disengage the fitting 147 and the valve mechanism 46 friction fit.

The blood receiving means 122 comprises the valve mechanism 46 that is now located at the top of riser tube R1 and the capillary tube 52 has been located between the two riser tubes R1 and R2. In addition, a vacutainer mechanism 101 has been added to the blood receiving means 122. The vacutainer mechanism 101 permits the retrieval of a sample of the first blood to reach the blood receiving means 122 for subsequent blood analysis (e.g., hematocrit studies). However, it should be understood that the vacutainer mechanism 101 does not form any part of the viscosity determination and does not impede, in any way, the operation of the DRSC viscometer 1020 in determining blood viscosity according to that described with respect to the embodiment 920. In fact, the vacutainer mechanism 101, as will be described below, disengages from the valve mechanism 46 before the viscosity test run begins.

Figure 17A:
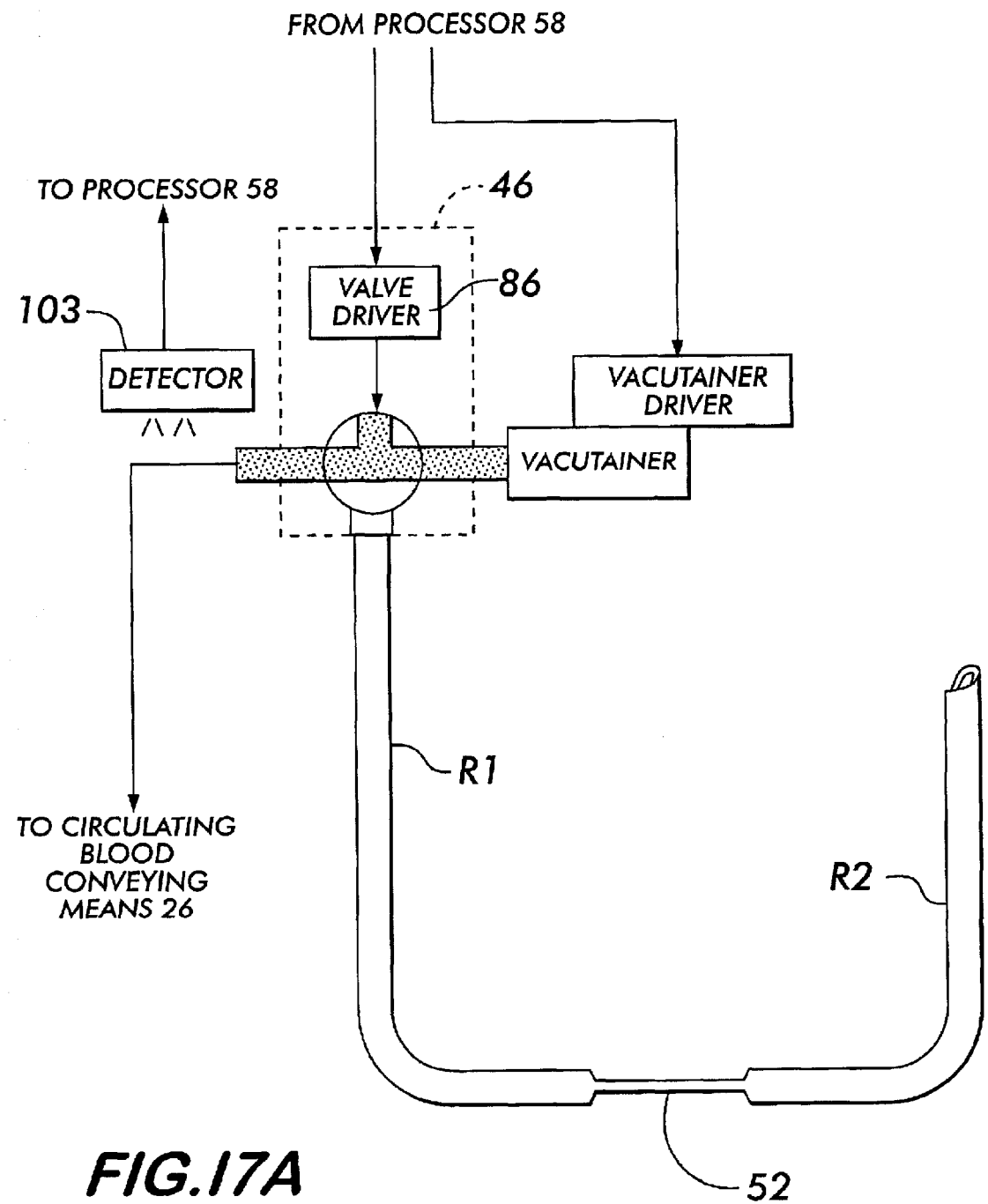
FIGS. 17A–17C depict the operation of the valve mechanism of the second embodiment of the DRSC viscometer just prior to, and during, the viscosity test run.

The vacutainer mechanism 101 comprises vacutainer 107 that is positionable by a vacutainer driver 109. Operation of the vacutainer mechanism 101 is depicted in FIGS. 15, 16, 17A–17B and flowcharts FIGS. 19A–19B. In particular, as shown most clearly in FIG. 17A, when the detector 103 (e.g., a photodetector, photo-eye, etc.) detects the first or initial portion of the input blood from the patient (via the CBCM 26), the detector 103 alerts the microprocessor 58 which activates the vacutainer driver 109 to drive the vacutainer 107 towards the puncturing means 111 (e.g., needle, FIG. 15) on the valve mechanism 46 which punctures a piercable surface of the vacutainer 107. Simultaneously, the processor 58 commands the valve driver 86 to place the valve in the first position (as shown in FIG. 17A). As a result, the first or initial portion of the input blood flow is captured in the vacutainer 107. After a fixed time, $t_p$, has elapsed, the processor 58 commands the vacutainer driver 109 to disengage the vacutainer 107 from the puncturing means 111.

With this initial portion of the input blood flow captured in the vacutainer 107, the operator can remove the vacutainer 107 from the driver 109 and then presented to a separate analyzing mechanism either on-site or remotely-located.

Figure 17B:
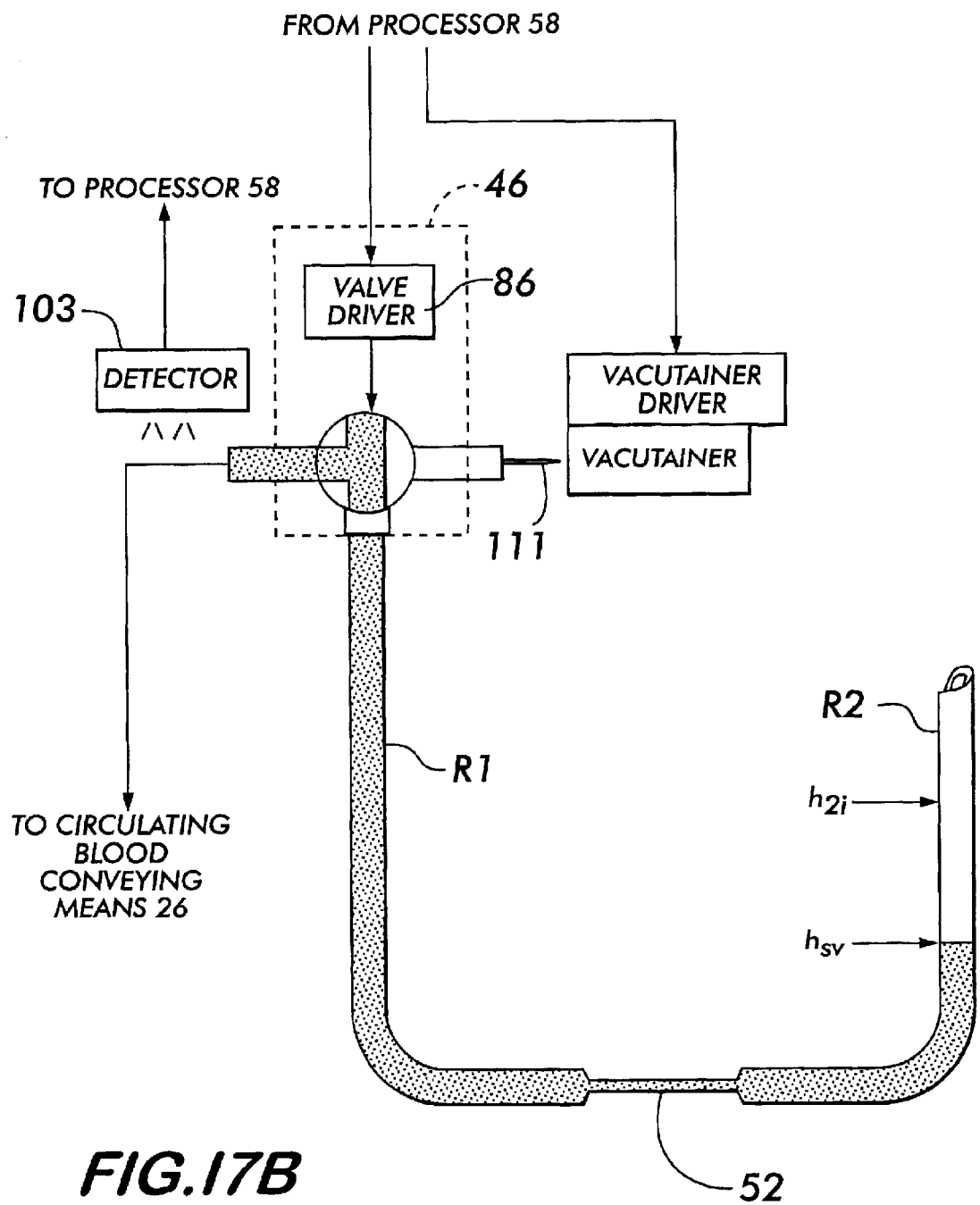
Figure 17C:
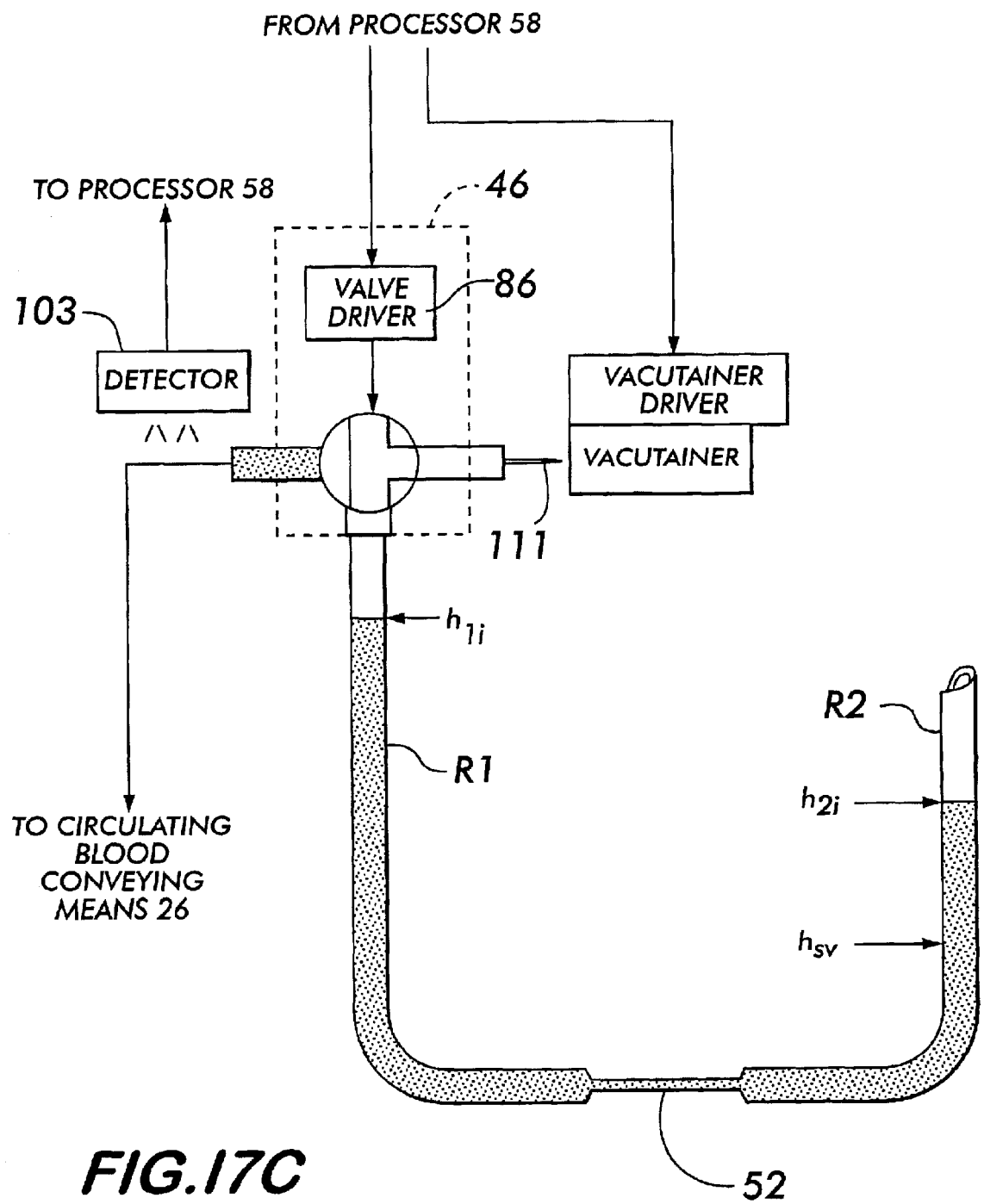

Simultaneous with the processor 58 commanding the vacutainer driver 109 to disengage the vacutainer 107 from the puncturing means 111, the processor 58 also commands the valve driver 86 to move the valve into the second position (FIG. 17B). As a result, the input blood flow enters into the top of the riser tube R2, down the riser tube R2, through the capillary 52 and up into riser tube R1. The column level detector 56 monitors the rising blood column in riser tube R2. When column level detector 56 detects a predetermined level, $h_{sv}$, it informs the processor 58. The $h_{SV}$ is an exact value that corresponds to an exact volume of blood such that when the column of blood in riser tube R2 reaches $h_{2i}$, (FIGS. 17B and 17C), the column of blood in riser R1 will be at $h_{1i}$. Therefore, when column level detector 56 detects that $h_{sv}$ has been reached, the processor 58 activates the valve driver 86 to rotate the valve into the third position (FIG. 17C), thereby isolating the two columns of blood from the input blood flow while simultaneously beginning the viscosity test run. This viscosity test run is similar to that described earlier with respect to embodiment 920 and, as such, will not be repeated here.

Alternatively, as mentioned earlier, the column level detector 56 can be used to detect the falling column of blood in the first riser tube R1 and the single point detector 954 can be used to detect the predetermined level, $h_{sv}$ of the rising column of blood in riser tube R2. Thus, it is within the broadest scope of the invention to cover the use of one column level detector for monitoring the change in position of the blood column in one riser tube and the use of a single point detector for detecting a single point of the blood column in the other riser tube.

It should be understood that any one point of the blood column can be detected by the single point detector 954. The preferred point is the initial column level for the viscosity test run, namely $h_{1i}$ or $h_{SV}$. However, any other point in the column can be detected in order to generate the corresponding height vs. time data/curve.

Figure 20:
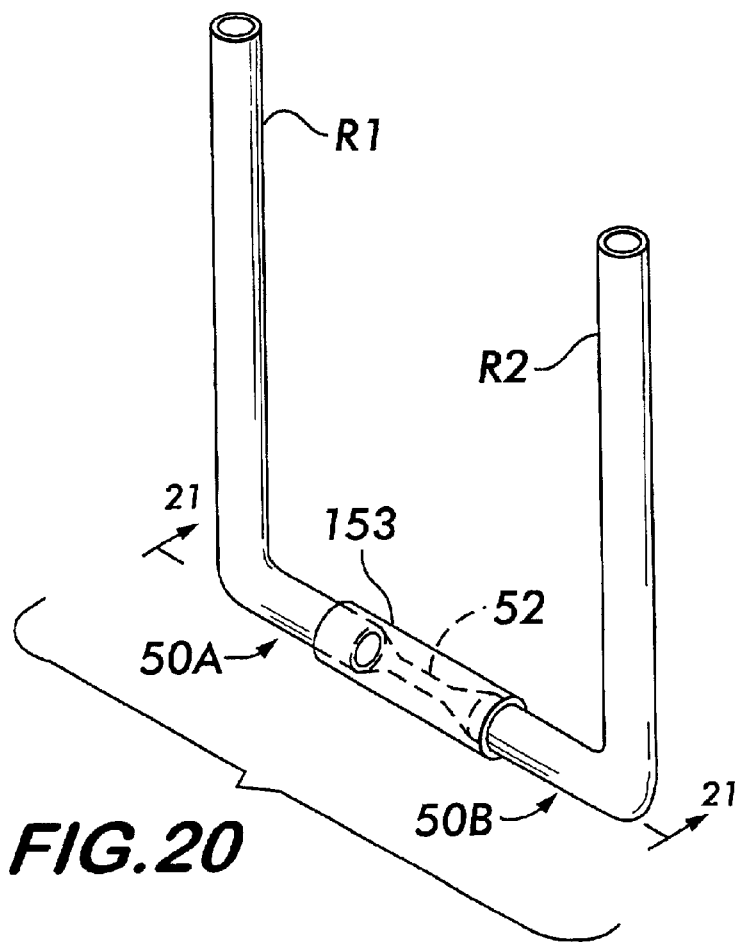
FIG. 20 depicts an implementation of the capillary and riser tube portion of the blood receiving means for the second embodiment of the DRSC viscometer.
Figure 21:
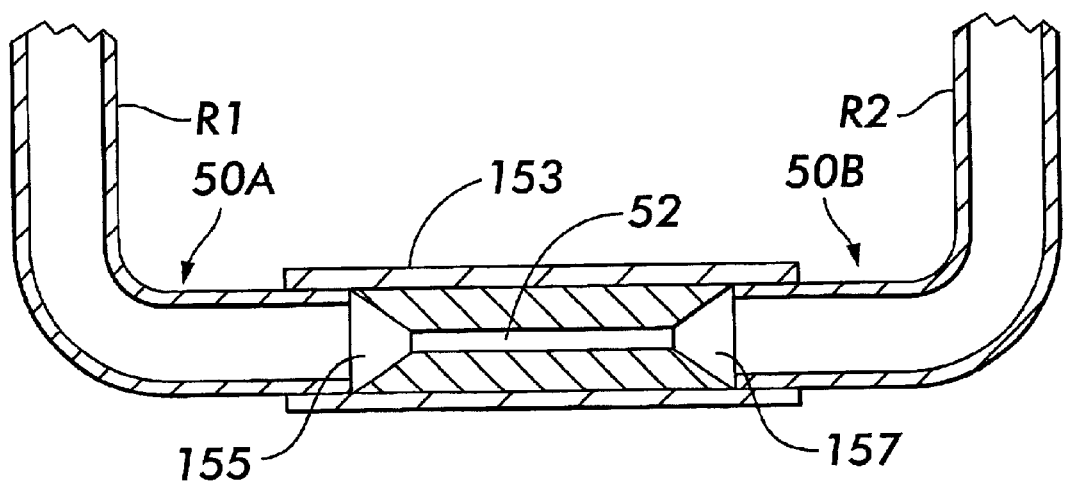
FIG. 21 is a partial cross-sectional view taken along line 21—21 of FIG. 20.

One exemplary implementation of the blood receiving means 122 is shown in FIGS. 20–21. In particular, the riser tubes R1 and R2 (e.g., injection-molded pieces) have integral elbows 50A and 50B that are inserted into respective ends of a capillary element 153. In particular, each end of the capillary element 153 forms a form fitting sleeve that slides over each end of the elbows 50A and 50B. As shown most clearly in FIG. 21, the capillary element 153 comprises a tapered entry port 155 and a tapered exit port 157 to minimize any turbulence as the circulating blood passes from the end of the elbow 50A into the capillary element 153 and then into the elbow 50B and up into riser tube R2.

It should be pointed out that the "blood receiving" means of all embodiments disclosed herein are merely exemplary of various combinations of components, such as riser tubes, etc., which can take various other forms than those specifically disclosed herein.

Figure 18:
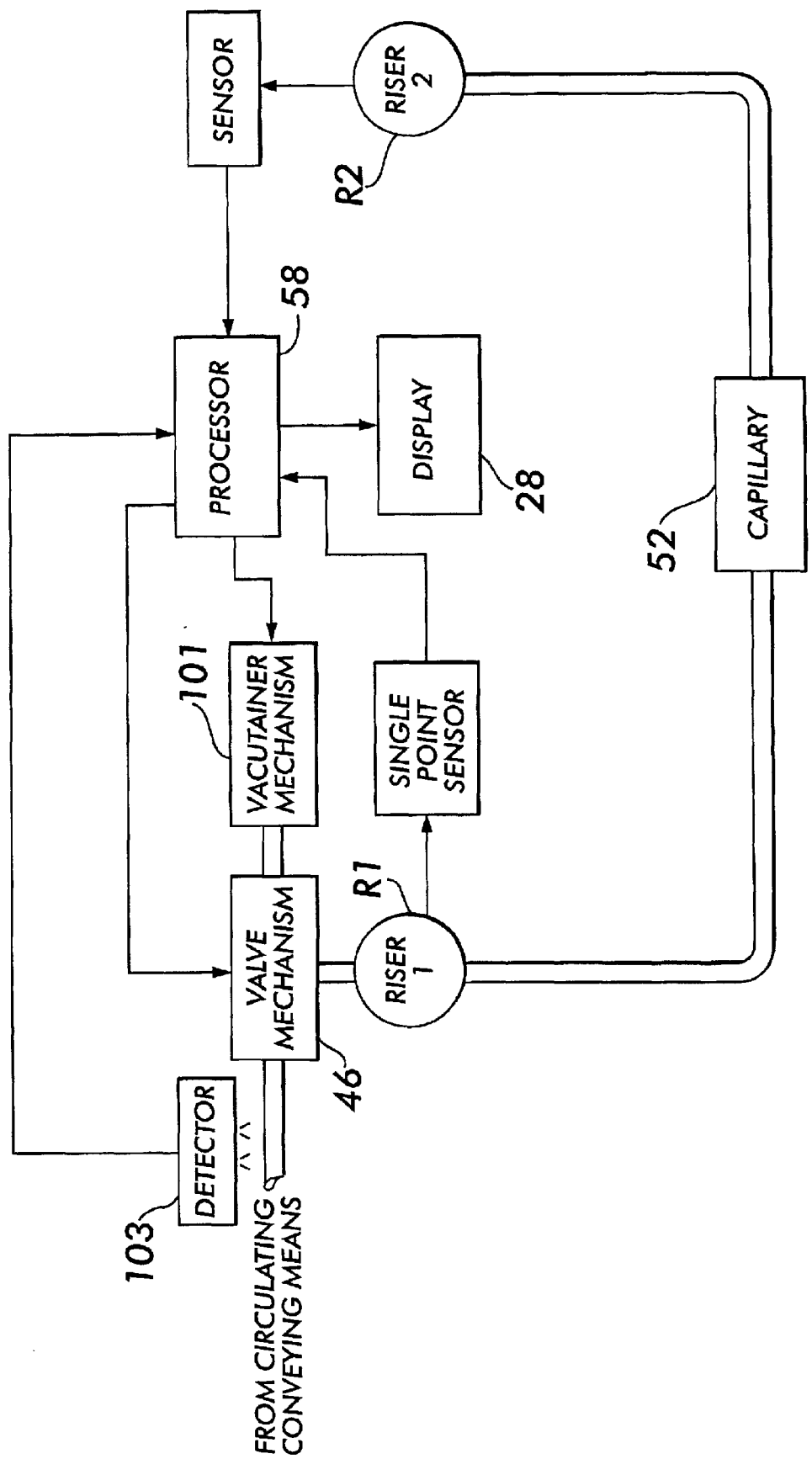
FIG. 18 is a block diagram for the second embodiment of the DRSC viscometer which detects movement of the column of fluid in each of the riser tubes using various types of sensors.

As shown in FIG. 18, it is within the broadest scope of the invention to include any means and/or method for monitoring the movement of either one of the columns of blood 82/84 in the riser tubes R1/R2 and for detecting the single point in the other one of the columns and, as such, are not limited to the LED array 64/CCD 66 arrangement for the column level detector 56, nor to the LED 964/photodetector 966 arrangement for the single point detector 954. In fact, the following type of physical detections (indicated by "SENSOR" in FIG. 8) are covered by the present invention:

d(Weight)/dt: the change in weight of either column of fluid with respect to time using a weight detecting means for each column of fluid as the sensor; e.g., $w_1(t)-w_2(t)$;

d(Pressure)/dt: the change in pressure of either column of fluid with respect to time using a pressure transducer located at the top of each column of fluid; e.g., $p_1(t)-p_2(t)$;

time of flight: the length of time it takes an acoustic signal to be emitted from a sensor (e.g., ultrasonic) located above either column of fluid and to be reflected and return to the sensor; e.g., time of flight$_1$(t)–time of flight$_2$(t);

d(Volume)/dt: the change in volume of either column of fluid with respect to time; e.g., $V_1(t)-V_2(t)$;

d(Position)/dt: the change in position of either column level using a digital video camera; e.g., $Pos_1(t)-Pos_2(t)$;

d(Mass)/dt: the change in mass with respect to time for either column of fluid; e.g., $m_1(t)-m_2(t)$.

The CCD 66 may be any conventional device. One particularly suitable one is available from ScanVision Inc. of San Jose, Calif. That CCD is of 300 dpi-83$\mu$ pixel resolution. The ScanVision Inc. CCD utilizes conventional CCD acquisition software. The LED arrays 64 can be implemented with a variety of light sources, including fiber optic lines.

Furthermore, the door 76 of the housing 60 can be configured to be hinged along the bottom of the housing 60 so as to swing down in order to gain access to the blood receiving means 22 or 122.

It should be understood that it is within the broadest scope of the invention 920 and 1020 to include auxiliary pressure (e.g., a pressure source such as a pump) as the motive force for moving the columns of blood 82/84 during the test run, as opposed to venting each of the riser tubes R1 and R2 to the ambient atmosphere.

It should be further understood that although the display 28 provides an efficient means for conveying the viscosity data to the user, the broadest scope of the DRSC viscometers 920 and 1020 does not require the display 28. Rather, as long as the viscosity data is available to any output means 30, the objectives of the present invention are met. Furthermore, it should be understood that the analyzer/output portion 924 in embodiments 920 and 1020 can accomplished by a any laptop personal computer and is not limited in any way by that which is depicted in FIGS. 2–3.

The blood receiving means 22 and 122 of the respective embodiments 920 and 1020 are typically located to be at a position that is lower than the patient's heart. By doing this, gravity assists the venous pressure in conveying the circulating blood to the blood receiving means 22/122, but this also prevents any backflow of blood into the patient during the preliminary hook up and viscosity test run.

Figure 19A:
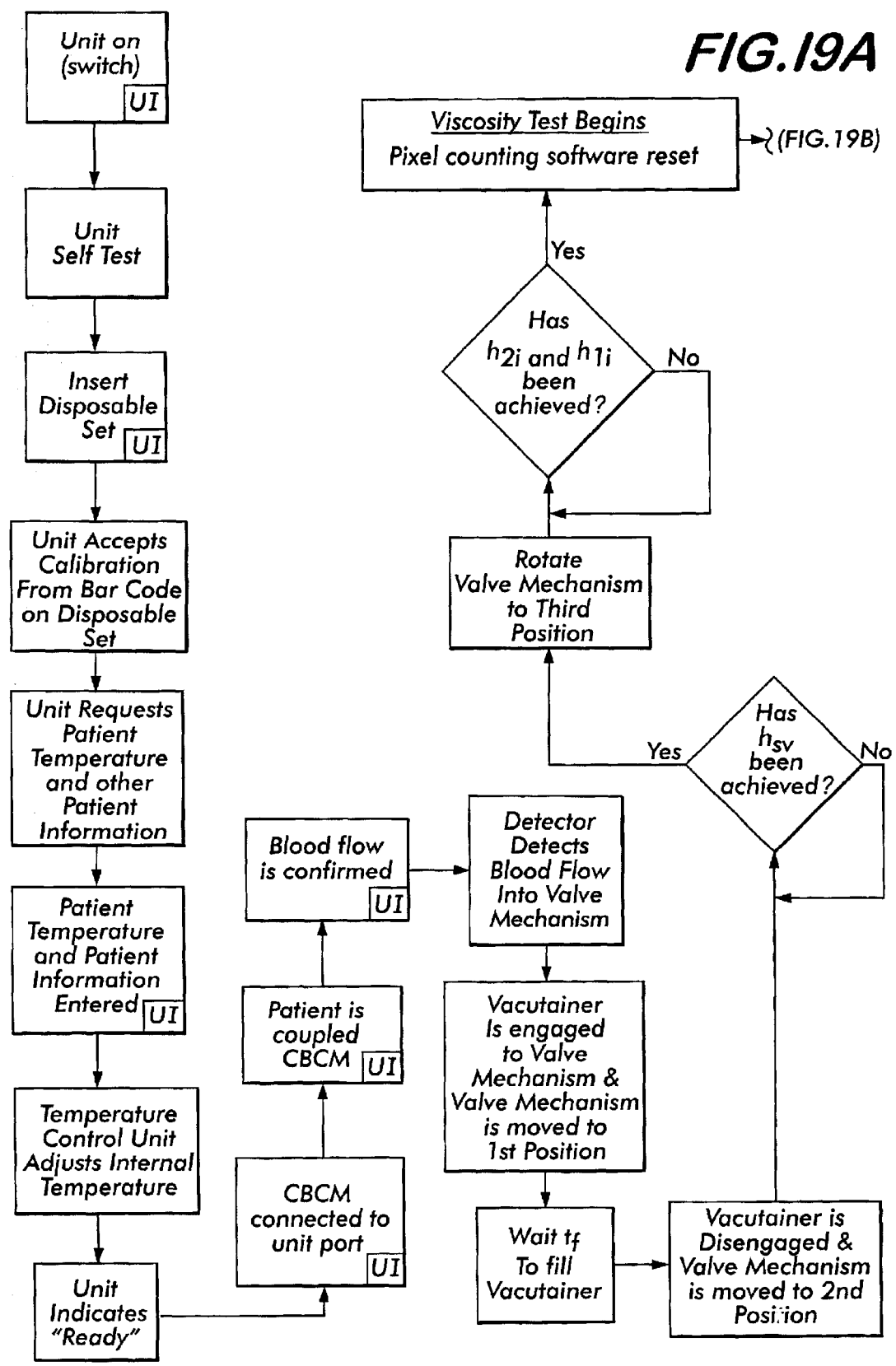
FIGS. 19A–19B comprise a flow chart of the operation of the second embodiment of the DRSC viscometer.
Figure 19B:
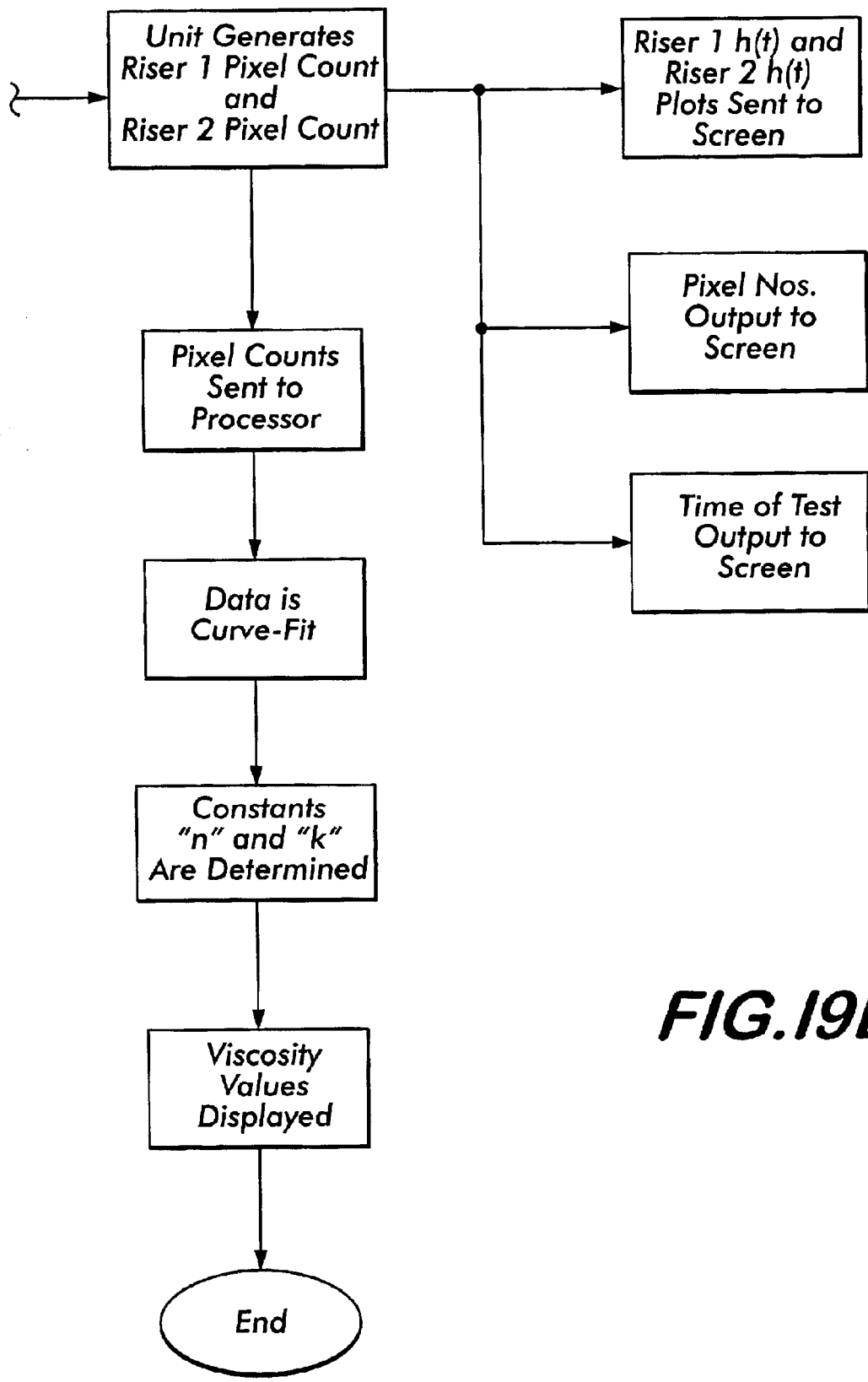

It should be understood that where a re-usable blood receiving means 22 is used in embodiment 920, or where a re-usable blood receiving means 122 is used in embodiment 1020, the step "insert disposable set" in FIG. 9B and FIG. 19B, respectively, is omitted.

It should also be noted that, as mentioned earlier, the preferred method/means is to monitor the rising column of blood 84 with the column level detector 56 as opposed to monitoring the falling column of blood 82 because a large amount of noise is encountered when the falling column 82 is monitored. The rising column 84 presents a more clean monitoring signal and is thus the preferred column to be monitored. However, it is within the broadest scope of this invention to include means for filtering or compensating this noise when the falling column is monitored by the column level detector 56.

Without further elaboration, the foregoing will so fully illustrate our invention and others may, by applying current or future knowledge, readily adapt the same for use under various conditions of service.

We claim:

1. An apparatus for detecting the movement of a fluid at plural shear rates using a decreasing pressure differential, said apparatus comprising:

a fluid source elevated above a horizontal reference position;

a capillary tube having a first end and a second end, said first end being in fluid communication with the fluid source through a first riser tube;

a second riser tube having one end coupled to said second end of said capillary tube and another end being exposed to atmospheric pressure, said second riser tube being positioned at an angle greater than zero degrees with respect to said horizontal reference position; and a respective sensor for detecting the movement of the fluid, caused by said decreasing pressure differential, through said first and second riser tubes, respectively, at plural shear rates as the fluid moves from the fluid source, through said first riser tube, through said capillary tube and into said second riser tube, said movement of fluid comprising a laminar flow.

2. The apparatus of claim 1 wherein one of said respective sensors monitors the laminar movement of the fluid over time in its respective riser tube and wherein the second one of said respective sensors detects a single data point of the laminar movement in its respective riser tube.

3. The apparatus of claim 1 wherein said second riser tube is positioned vertically with respect to said horizontal reference position.

4. The apparatus of claim 3 wherein said movement of the fluid through said riser tubes comprises:
   a rising fluid column in said second riser tube and wherein its corresponding sensor monitors the changing height of said rising column fluid over time, said height being defined as the distance between the top of said rising fluid column and said horizontal reference position; and
   a falling fluid column in said first riser tube and wherein its corresponding sensor detects a single data point of said falling fluid column.

5. The apparatus of claim 1 wherein the fluid is a non-Newtonian fluid.

6. The apparatus of claim 1 wherein said capillary tube comprises capillary tube dimensions and said first and second riser tubes comprise a riser tube dimension, said apparatus further comprising a computer, said computer being coupled to said respective sensors for receiving fluid movement data from said sensors and wherein said computer calculates the viscosity of the fluid based on said capillary tube dimensions, said riser tube dimension and said fluid movement data.

7. The apparatus of claim 6 wherein one of said respective sensors monitors the laminar movement of the fluid over time in its respective riser tube and wherein the second one of said respective sensors detects a single data point of the laminar movement in its respective riser tube.

8. The apparatus of claim 7 wherein said movement of the fluid through said riser tubes comprises:
   a rising fluid column in said second riser tube and wherein its corresponding sensor monitors the changing height of said rising fluid column over time, said height being defined as the distance between the top of said rising fluid column and said horizontal reference position;
   a falling fluid column in said first riser tube and wherein its corresponding sensor detects a single data point of said falling fluid column; and
   said monitored changing height of said rising fluid column and said single data point of said falling fluid column forming said fluid movement data.

9. The apparatus of claim 6 wherein said second riser tube is positioned vertically with respect to said horizontal reference position.

10. The apparatus of claim 6 wherein the fluid is a non-Newtonian fluid.

11. An apparatus for determining the viscosity of a non-Newtonian fluid over plural shear rates using a decreasing pressure differential, said apparatus comprising:
   a non-Newtonian fluid source elevated above a horizontal reference position;
   a capillary tube having a first end and a second end, said first end being coupled to the non-Newtonian fluid source through a first riser tube, said capillary tube having capillary tube dimensions;
   a second riser tube having one end coupled to said first end of said capillary tube and another end being exposed to atmospheric pressure, said second riser tube being positioned at an angle greater than zero degrees with respect to said horizontal reference position, said first and second riser tubes comprising a riser tube dimension;
   a respective sensor for detecting the movement of the non-Newtonian fluid, caused by said decreasing pressure differential, through said first and second riser tubes, respectively, at plural shear rates as the non-Newtonian fluid moves from the non-Newtonian fluid source, through said first riser tube, through said capillary tube and into said second riser tube in a laminar flow, said sensors generating data relating to the movement of the non-Newtonian fluid over time; and
   a computer, coupled to said sensors, for calculating the viscosity of the non-Newtonian fluid based on said data relating to the movement of the non-Newtonian fluid over time, said capillary tube dimensions and said riser tube dimension.

12. The apparatus of claim 11 wherein one of said respective sensors monitors the laminar movement of the fluid over time in its respective riser tube and wherein the second one of said respective sensors detects a single data point of the laminar movement in its respective riser tube.

13. The apparatus of claim 11 wherein said riser tube is positioned vertically with respect to said horizontal reference position.

14. The apparatus of claim 13 wherein said movement of the fluid through said riser tubes comprises:
   a rising fluid column in said second riser tube and wherein its corresponding sensor monitors the changing height of said rising fluid column over time, said height being defined as the distance between the top of said rising fluid column and said horizontal reference position;
   a falling fluid column in said first riser tube and wherein its corresponding sensor detects a single data point of said falling fluid column; and
   said monitored changing height of said rising fluid column and said single data point of said falling fluid column forming said fluid movement data.

15. The apparatus of claim 11 wherein said non-Newtonian fluid is the circulating blood of a living being and the non-Newtonian fluid source is the vascular system of the living being.

16. An apparatus for detecting the movement of a fluid at plural shear rates using a decreasing pressure differential, said apparatus comprising:
   a fluid source elevated above a horizontal reference position;
   a first riser tube having a first end exposed to atmospheric pressure and a second end, said second end being in fluid communication with the fluid source for generating a first fluid column in said first riser tube;
   a capillary tube having a first capillary tube end and a second capillary tube end, said first capillary tube end being in fluid communication with the fluid source;
   a second riser tube having one end coupled to said second capillary end and another end being exposed to atmospheric pressure for generating a second fluid column in said second riser tube, said second riser tube being positioned at an angle greater than zero degrees with respect to said horizontal reference position, and wherein a second fluid column is generated in said second riser tube; and
   a respective sensor for detecting the movement of the fluid in said riser tubes, caused by said decreasing pressure differential when said second end of said first riser tube and said first capillary tube end are placed into fluid communication with each other, said movement of fluid from said first riser tube, through said capillary tube and into said second riser tube at plural shear rates forming a laminar flow.

17. The apparatus of claim 16 wherein one of said respective sensors monitors the laminar movement of the fluid over time in its respective riser tube and wherein the second one of said respective sensors detects a single data point of the laminar movement in its respective riser tube.

18. The apparatus of claim 16 wherein said second riser tube is positioned vertically with respect to said horizontal reference position.

19. The apparatus of claim 18 wherein said movement of the fluid through said riser tubes comprises:

a rising fluid column in said second riser tube and wherein its corresponding sensor monitors the changing height of said rising column fluid over time, said height being defined as the distance between the top of said rising fluid column and said horizontal reference position; and a falling fluid column in said first riser tube and wherein its corresponding sensor detects a single data point of said falling fluid column.

20. The apparatus of claim 16 wherein the fluid is a non-Newtonian fluid.

21. The apparatus of claim 16 wherein said capillary tube comprises capillary tube dimensions and said first and second riser tubes comprise a riser tube dimension, said apparatus further comprising a computer, said computer being coupled to said respective sensors for receiving fluid movement data from said sensors and wherein said computer calculates the viscosity of the fluid based on said capillary tube dimensions, said riser tube dimension and said fluid movement data.

22. The apparatus of claim 21 wherein one of said respective sensors monitors the laminar movement of the fluid over time in its respective riser tube and wherein the second one of said respective sensors detects a single data point of the laminar movement in its respective riser tube.

23. The apparatus of claim 22 wherein said movement of the fluid through said riser tubes comprises:

a rising fluid column in said second riser tube and wherein its corresponding sensor monitors the changing height of said rising fluid column over time, said height being defined as the distance between the top of said rising fluid column and said horizontal reference position;

a falling fluid column in said first riser tube and wherein its corresponding sensor detects a single data point of said falling fluid column; and said monitored changing height of said rising fluid column and said single data point of said falling fluid column forming said fluid movement data.

24. The apparatus of claim 21 wherein said second riser tube is positioned vertically with respect to said horizontal reference position.

25. The apparatus of claim 21 wherein the fluid is a non-Newtonian fluid.

26. An apparatus for determining the viscosity of a non-Newtonian fluid over plural shear rates using a decreasing pressure differential, said apparatus comprising:

a non-Newtonian fluid source elevated above a horizontal reference position;

a first riser tube having a first end exposed to atmospheric pressure and a second end, said second end being in fluid communication with the non-Newtonian fluid source for generating a first fluid column in said first riser tube;

a capillary tube having a first capillary tube end and a second capillary tube end, said first capillary tube end being in fluid communication with the non-Newtonian fluid source, said capillary tube having capillary tube dimensions;

a second riser tube having one end coupled to said second capillary tube end and another end being exposed to atmospheric pressure for generating a second fluid column in said second riser tube, said second riser tube being positioned at an angle greater than zero degrees with respect to said horizontal reference position, said first and second riser tubes comprising a riser tube dimension;

a respective sensor for detecting the movement of the non-Newtonian fluid, caused by said decreasing pressure differential when said second end of said first riser tube and said first capillary tube end are placed into fluid communication with each other, said movement of fluid from said first riser tube, through said capillary tube and into said second riser tube at plural shear rates forming a laminar flow, said sensors generating data relating to the movement of the non-Newtonian fluid over time; and a computer, coupled to said sensors, for calculating the viscosity of the non-Newtonian fluid based on said data relating to the movement of the non-Newtonian fluid over time, said capillary tube dimensions and said riser tube dimension.

27. The apparatus of claim 26 wherein one of said respective sensors monitors the laminar movement of the fluid over time in its respective riser tube and wherein the second one of said respective sensors detects a single data point of the laminar movement in its respective riser tube.

28. The apparatus of claim 26 wherein said riser tube is positioned vertically with respect to said horizontal reference position.

29. The apparatus of claim 28 wherein said movement of the fluid through said riser tubes comprises:

a rising fluid column in said second riser tube and wherein its corresponding sensor monitors the changing height of said rising fluid column over time, said height being defined as the distance between the top of said rising fluid column and said horizontal reference position;

a falling fluid column in said first riser tube and wherein its corresponding sensor detects a single data point of said falling fluid column; and said monitored changing height of said rising fluid column and said single data point of said falling fluid column forming said fluid movement data.

30. The apparatus of claim 26 wherein said non-Newtonian fluid is the circulating blood of a living being and the non-Newtonian fluid source is the vascular system of the living being.

* * * * *

UNITED STATES PATENT AND TRADEMARK OFFICE
CERTIFICATE OF CORRECTION

PATENT NO. : 6,745,615 B2  
DATED : June 8, 2004  
INVENTOR(S) : Kensey et al.

It is certified that error appears in the above-identified patent and that said Letters Patent is hereby corrected as shown below:

Column 19,
Line 61, replace the word "first" with -- second --.

Signed and Sealed this

Eighth Day of February, 2005

JON W. DUDAS
*Director of the United States Patent and Trademark Office*